United States Patent
Duffill et al.

(10) Patent No.: US 7,974,792 B2
(45) Date of Patent: Jul. 5, 2011

(54) METER ELECTRONICS AND METHODS FOR DETERMINING A LIQUID FLOW FRACTION IN A GAS FLOW MATERIAL

(75) Inventors: Graeme Ralph Duffill, Boulder, CO (US); Steven M. Jones, Erie, CO (US); Andrew Timothy Patten, Boulder, CO (US)

(73) Assignee: Micro Motion, Inc., Boulder, CO (US)

( * ) Notice: Subject to any disclaimer, the term of this patent is extended or adjusted under 35 U.S.C. 154(b) by 238 days.

(21) Appl. No.: 11/908,391

(22) PCT Filed: Mar. 15, 2006

(86) PCT No.: PCT/US2006/009272
§ 371 (c)(1),
(2), (4) Date: Sep. 11, 2007

(87) PCT Pub. No.: WO2006/104690
PCT Pub. Date: Oct. 5, 2006

(65) Prior Publication Data
US 2008/0190195 A1    Aug. 14, 2008

Related U.S. Application Data

(60) Provisional application No. 60/666,023, filed on Mar. 29, 2005.

(51) Int. Cl.
*G01F 1/00* (2006.01)
(52) U.S. Cl. ......... 702/45; 73/61.44; 73/861.04; 702/50
(58) Field of Classification Search ............ 702/45, 702/48, 50, 54, 56, 137; 73/861.01, 861.04, 73/861.18, 200, 61.44
See application file for complete search history.

(56) References Cited

U.S. PATENT DOCUMENTS

| | | | |
|---|---|---|---|
| 4,773,257 A | 9/1988 | Aslesen et al. | |
| 4,996,871 A | 3/1991 | Romano | |
| 5,029,482 A | 7/1991 | Liu et al. | |
| 5,259,250 A | 11/1993 | Kolpak | |
| 5,535,632 A * | 7/1996 | Kolpak | 73/861.04 |
| 5,578,764 A | 11/1996 | Yokoi et al. | |
| 6,311,136 B1 | 10/2001 | Henry et al. | |
| 6,318,156 B1 * | 11/2001 | Dutton et al. | 73/61.44 |
| 7,062,976 B2 * | 6/2006 | Gysling et al. | 73/861.18 |
| 7,117,104 B2 * | 10/2006 | Urdaneta et al. | 702/48 |
| 2004/0221660 A1 | 11/2004 | Dutton et al. | |

FOREIGN PATENT DOCUMENTS
GB    1219887    1/1971

(Continued)

*Primary Examiner* — John H Le
(74) *Attorney, Agent, or Firm* — The Ollila Law Group LLC

(57) ABSTRACT

Meter electronics (20) for determining a liquid flow fraction in a gas flow material flowing through a flow meter (5) is provided according to an embodiment of the invention. The meter electronics (20) includes an interface (201) for receiving a first sensor signal and a second sensor signal from the flow meter (5) and a processing system (203) in communication with the interface (201). The processing system (203) is configured to receive the first and second sensor signals from the interface (201), determine a substantially instantaneous flow stream density of the gas flow material using the first sensor signal and the second sensor signal, compare the substantially instantaneous flow stream density to at least one of a predetermined gas density that is representative of a gas flow fraction of the gas flow material and a predetermined liquid density that is representative of a liquid flow fraction, and determine the liquid flow fraction from the comparison.

26 Claims, 16 Drawing Sheets

FOREIGN PATENT DOCUMENTS

| | | |
|---|---|---|
| JP | 10281846 A | 10/1998 |
| JP | 2007181069 A | 7/2007 |
| RU | 2102708 C1 | 1/1998 |
| WO | WO9308452 | 4/1993 |
| WO | WO-02/060805 A2 | 8/2002 |
| WO | 03021204 A1 | 3/2003 |

* cited by examiner

METER ELECTRONICS AND METHODS FOR DETERMINING A LIQUID FLOW FRACTION IN A GAS FLOW MATERIAL

The present application claims the benefit of PCT Patent Application No. PCT/US06/09272, entitled "Meter Electronics and Methods for Determining a Liquid Flow Fraction in a Gas Flow Material", filed on Mar. 15, 2006, which claims benefit of U.S. Provisional Patent Application No. 60/666, 023, entitled "Meter Electronics and Methods for Determining A Liquid Flow Fraction in a Gas Flow Material", filed on Mar. 29, 2005.

BACKGROUND OF THE INVENTION

1. Field of the Invention

The present invention relates to meter electronics and methods for determining a liquid flow fraction in a gas flow material flowing through a flow meter.

2. Statement of the Problem

It is known to use Coriolis mass flow meters to measure mass flow and other information of materials flowing through a pipeline as disclosed in U.S. Pat. No. 4,491,025 issued to J. E. Smith, et al. of Jan. 1, 1985 and U.S. Pat. No. Re. 31,450 to J. E. Smith of Feb. 11, 1982. These flow meters have one or more flow tubes of different configurations. Each conduit configuration may be viewed as having a set of natural vibration modes including, for example, simple bending, torsional, radial and coupled modes. In a typical Coriolis mass flow measurement application, a conduit configuration is excited in one or more vibration modes as a material flows through the conduit, and motion of the conduit is measured at points spaced along the conduit.

The vibrational modes of the material filled systems are defined in part by the combined mass of the flow tubes and the material within the flow tubes. Material flows into the flow meter from a connected pipeline on the inlet side of the flow meter. The material is then directed through the flow tube or flow tubes and exits the flow meter to a pipeline connected on the outlet side.

A driver applies a force to the flow tube. The force causes the flow tube to oscillate. When there is no material flowing through the flow meter, all points along a flow tube oscillate with an identical phase. As a material begins to flow through the flow tube, Coriolis accelerations cause each point along the flow tube to have a different phase with respect to other points along the flow tube. The phase on the inlet side of the flow tube lags the driver, while the phase on the outlet side leads the driver. Sensors are placed at different points on the flow tube to produce sinusoidal signals representative of the motion of the flow tube at the different points. The phase difference between the two sensor signals is proportional to the mass flow rate of the material flowing through the flow tube or flow tubes. In one prior art approach either a Discrete Fourier Transform (DFT) or a Fast Fourier Transform (FFT) is used to determine the phase difference between the sensor signals. The phase difference and a vibrational frequency response of the flow tube assembly are used to obtain the mass flow rate.

In one prior art approach, an independent reference signal is used to determine a pickoff signal frequency, such as by using the frequency sent to the vibrational driver system. In another prior art approach, the vibrational response frequency generated by a pickoff sensor can be determined by centering to that frequency in a notch filter, wherein the prior art flowmeter attempts to keep the notch of the notch filter at the pickoff sensor frequency. This prior art technique works fairly well under quiescent conditions, where the flow material in the flowmeter is uniform and where the resulting pickoff signal frequency is relatively stable. However, the phase measurement of the prior art suffers when the flow material is not uniform, such as in two-phase flows where the flow material comprises a gas flow material that includes entrained liquid. In such situations, the prior art determined frequency can fluctuate rapidly. During conditions of fast and large frequency transitions, it is possible for the pickoff signals to move outside the filter bandwidth, yielding incorrect phase and frequency measurements. This also is a problem in empty-full-empty batching, where the flow meter is repeatedly operated in alternating empty and full conditions. Also, if the frequency of the sensor moves rapidly, a demodulation process will not be able to keep up with the actual or measured frequency, causing demodulation at an incorrect frequency. It should be understood that if the determined frequency is incorrect or inaccurate, then subsequently derived values of density, volume flow rate, etc., will also be incorrect and inaccurate. Moreover, the error can be compounded in subsequent flow characteristic determinations.

In the prior art, the pickoff signals can be digitized and digitally manipulated in order to implement the notch filter. The notch filter accepts only a narrow band of frequencies. Therefore, when the target frequency is changing, the notch filter may not be able to track the target signal for a period of time. Typically, the digital notch filter implementation takes 1-2 seconds to track to the fluctuating target signal. Due to the time required by the prior art to determine the frequency, the result is not only that the frequency and phase determinations contain errors, but also that the error measurement encompasses a time span that exceeds the time span during which the error and/or two-phase flow actually occur. This is due to the relative slowness of response of a notch filter implementation.

The result is that the prior art flowmeter cannot accurately, quickly, or satisfactorily track or determine a pickoff sensor frequency during two-phase flow of the flow material in the flowmeter. Consequently, the phase determination is likewise slow and error prone, as the prior art derives the phase difference using the determined pickoff frequency. Therefore, any error in the frequency determination is compounded in the phase determination. The result is increased error in the frequency determination and in the phase determination, leading to increased error in determining the mass flow rate. In addition, because the determined frequency value is used to determine a density value (density is approximately equal to one over frequency squared), an error in the frequency determination is repeated or compounded in the density determination. This is also true for a determination of volume flow rate, where the volume flow rate is equal to mass flow rate divided by density.

One application of a vibrating flow tube device as described above is in measuring a mass flow rate of a gas flow material. A typical application is the measurement of gas production from a well, such as natural gas, for example. However, the gas from a well typically does not exist in a pure state, and contains varying amounts of impurities, such as water, for example. Therefore, the gas flow material can contain a mixture of gas and liquid or liquid particles. This two-phase flow makes production measurement difficult. In addition, in natural gas production, the gas may be passed through a separator that uses glycol (or other drying liquid) to remove water from the gas flow material. However, this drying process can result in some of the drying liquid becoming entrained in the gas flow material. This is termed liquid flow fraction, wherein the gas flow material includes some liquid or liquid particles. Measurement of a gas flow material that includes liquid flow fraction is problematic.

A prior art approach to measuring a gas flow including a liquid flow fraction is to measure an average density. The prior art can determine when the density has deviated from an essentially pure gas flow and disregard density information when a detectable amount of liquid is entrained in the gas flow. Alternatively, the prior art can correlate the average flow density to known values in order to obtain an average gas flow fraction amount.

However, this prior art approach has drawbacks. The average gas mass flow rate is not highly accurate in many settings, such as where the amount of liquid flow fraction is fluctuating.

SUMMARY OF THE SOLUTION

The above and other problems are solved and an advance in the art is achieved through the provision of meter electronics and methods for determining a liquid flow fraction in a gas flow material flowing through a flow meter.

Meter electronics for determining a liquid flow fraction in a gas flow material flowing through a flow meter is provided according to an embodiment of the invention. The meter electronics comprises an interface for receiving a first sensor signal and a second sensor signal from the flow meter and a processing system in communication with the interface. The processing system is configured to receive the first and second sensor signals from the interface, determine a substantially instantaneous flow stream density of the gas flow material using the first sensor signal and the second sensor signal, compare the substantially instantaneous flow stream density to at least one of a predetermined gas density that is representative of a gas flow fraction of the gas flow material and a predetermined liquid density that is representative of a liquid flow fraction, and determine the liquid flow fraction from the comparison.

Meter electronics for determining a liquid flow fraction in a gas flow material flowing through a flow meter is provided according to an embodiment of the invention. The meter electronics comprises an interface for receiving a first sensor signal and a second sensor signal from the flow meter and a processing system in communication with the interface. The processing system is configured to receive the first and second sensor signals from the interface, generate a 90 degree phase shift from the first sensor signal, compute a frequency response using the 90 degree phase shift and the first sensor signal, determine a flow stream density of the gas flow material using the frequency response, and determine the liquid flow fraction from the flow stream density.

A method for determining a liquid flow fraction in a gas flow material flowing through a flow meter is provided according to an embodiment of the invention. The method comprises receiving a first sensor signal and a second sensor signal from the flow meter, determining a substantially instantaneous flow stream density of the gas flow material using the first sensor signal and the second sensor signal, comparing the substantially instantaneous flow stream density to at least one of a predetermined gas density that is representative of a gas flow fraction of the gas flow material and a predetermined liquid density that is representative of a liquid flow fraction, and determining the liquid flow fraction from the comparing.

A method for determining a liquid flow fraction in a gas flow material flowing through a flow meter is provided according to an embodiment of the invention. The method comprises receiving a first sensor signal and a second sensor signal from the flow meter, generating a 90 degree phase shift from the first sensor signal, computing a frequency response using the 90 degree phase shift and the first sensor signal, determining a flow stream density of the gas flow material using the frequency response, and determining the liquid flow fraction from the flow stream density.

ASPECTS OF THE INVENTION

In one aspect of the meter electronics, the processing system is further configured to determine the gas flow fraction.

In another aspect of the meter electronics, the processing system is further configured to generate a 90 degree phase shift from the first sensor signal, compute a frequency response using the 90 degree phase shift and the first sensor signal, and determine the substantially instantaneous flow stream density using the frequency response.

In yet another aspect of the meter electronics, the processing system is further configured to determine the flow stream density by squaring the frequency response to generate a squared frequency response and inverting the squared frequency response to generate the flow stream density.

In yet another aspect of the meter electronics, the processing system is further configured to generate a 90 degree phase shift from the first sensor signal, compute a frequency response using the 90 degree phase shift and the first sensor signal, square the frequency response to generate a squared frequency response, and invert the squared frequency response to generate the substantially instantaneous flow stream density of the gas flow material.

In yet another aspect of the meter electronics, the processing system is further configured to compare the liquid flow fraction to a predetermined liquid fraction threshold and set an alarm condition if the liquid flow fraction exceeds the predetermined liquid fraction threshold.

In yet another aspect of the meter electronics, the processing system is further configured to determine a flow stream density of the gas flow material from the first sensor signal and the second sensor signal, compare the flow stream density to at least one of a predetermined gas density that is representative of a gas flow fraction of the gas flow material and a predetermined liquid density that is representative of a liquid flow fraction, and determine the liquid flow fraction from the comparison.

In yet another aspect of the meter electronics, the comparing further comprises comparing the substantially instantaneous flow stream density to a drive gain and to at least one of a predetermined gas density that is representative of a gas flow fraction of the gas flow material and a predetermined liquid density that is representative of a liquid flow fraction.

In yet another aspect of the meter electronics, the determining the liquid flow fraction further comprises determining the liquid flow fraction from the flow stream density and a drive gain.

In yet another aspect of the meter electronics, the flow meter comprises a Coriolis flow meter.

In yet another aspect of the meter electronics, the flow meter comprises a vibrating densitometer.

In one aspect of the method, the method further comprises determining the gas flow fraction.

In another aspect of the method, the method further comprises generating a 90 degree phase shift from the first sensor signal, computing a frequency response using the 90 degree phase shift and the first sensor signal, and determining the substantially instantaneous flow stream density from the frequency response.

In yet another aspect of the method, the method further comprises squaring the frequency response to generate a squared frequency response and inverting the squared frequency response to generate the substantially instantaneous flow stream density.

In yet another aspect of the method, the method further comprises comparing the liquid flow fraction to a predetermined liquid fraction threshold and setting an alarm condition if the liquid flow fraction exceeds the predetermined liquid fraction threshold.

In yet another aspect of the method, the determining the liquid flow fraction further comprises comparing the flow stream density to at least one of a predetermined gas density that is representative of a gas flow fraction of the gas flow material and a predetermined liquid density that is representative of a liquid flow fraction and determining the liquid flow fraction from the comparing.

In yet another aspect of the method, the determining the liquid flow fraction further comprises determining the liquid flow fraction from the flow stream density and a drive gain.

In yet another aspect of the method, the comparing further comprises comparing the substantially instantaneous flow stream density to a drive gain and to at least one of a predetermined gas density that is representative of a gas flow fraction of the gas flow material and a predetermined liquid density that is representative of a liquid flow fraction.

DESCRIPTION OF THE DRAWINGS

The same reference number represents the same element on all drawings.

DETAILED DESCRIPTION OF THE INVENTION

FIGS. 1-17 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
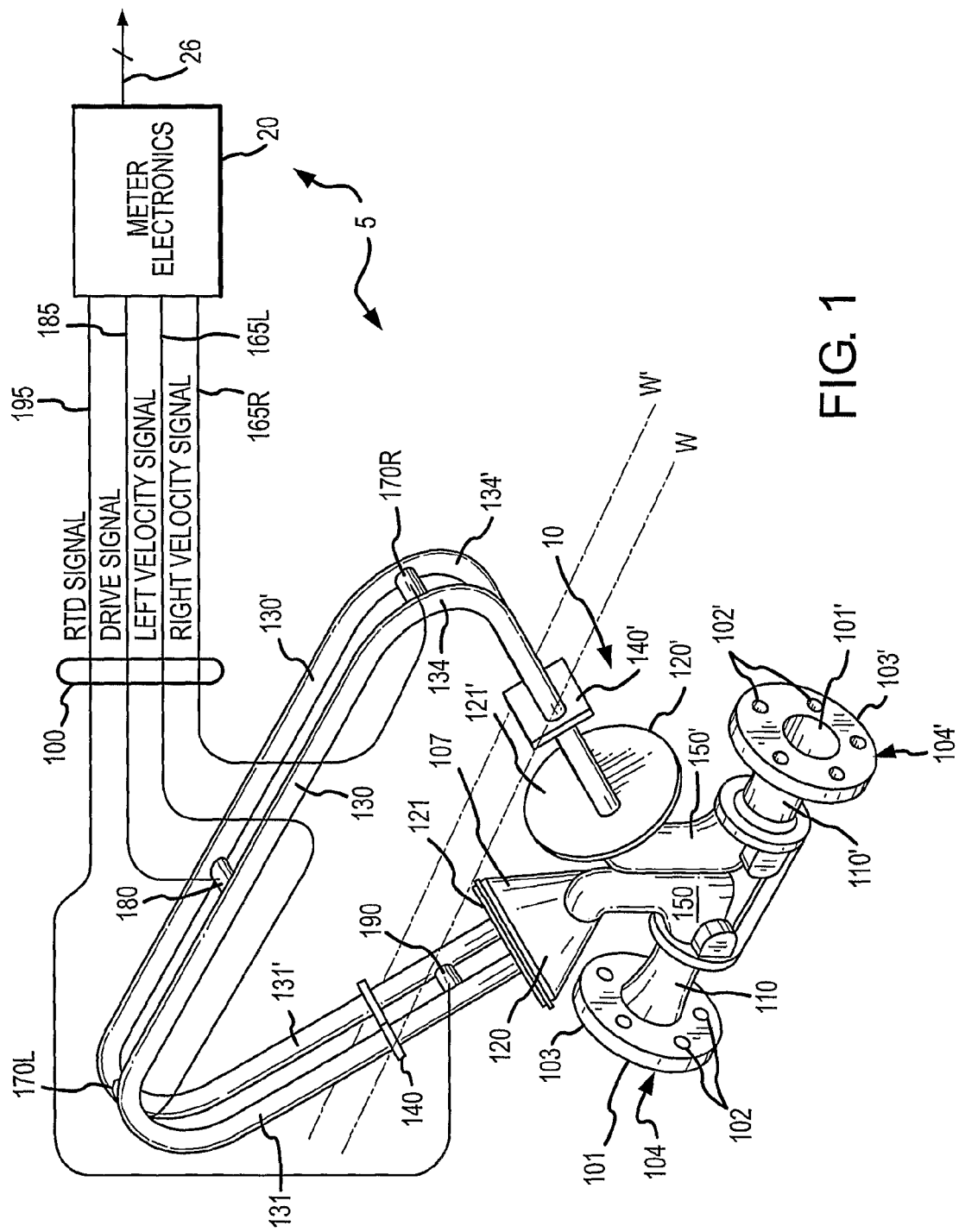
FIG. 1 illustrates a Coriolis flow meter in an example of the invention.

FIG. 1 shows a Coriolis flow meter 5 comprising a meter assembly 10 and meter electronics 20. Meter assembly 10 responds to mass flow rate and density of a process material. Meter electronics 20 is connected to meter assembly 10 via leads 100 to provide density, mass flow rate, and temperature information over path 26, as well as other information not relevant to the present invention. A Coriolis flow meter structure is described although it is apparent to those skilled in the art that the present invention could be practiced as a vibrating tube densitometer without the additional measurement capability provided by a Coriolis mass flow meter.

Meter assembly 10 includes a pair of manifolds 150 and 150', flanges 103 and 103' having flange necks 110 and 110', a pair of parallel flow tubes 130 and 130', drive mechanism 180, temperature sensor 190, and a pair of velocity sensors 170L and 170R. Flow tubes 130 and 130' have two essentially straight inlet legs 131 and 131' and outlet legs 134 and 134' which converge towards each other at flow tube mounting blocks 120 and 120'. Flow tubes 130 and 130' bend at two symmetrical locations along their length and are essentially parallel throughout their length. Brace bars 140 and 140' serve to define the axis W and W' about which each flow tube oscillates.

The side legs 131, 131' and 134, 134' of flow tubes 130 and 130' are fixedly attached to flow tube mounting blocks 120 and 120' and these blocks, in turn, are fixedly attached to manifolds 150 and 150'. This provides a continuous closed material path through Coriolis meter assembly 10.

When flanges 103 and 103', having holes 102 and 102' are connected, via inlet end 104 and outlet end 104' into a process line (not shown) which carries the process material that is being measured, material enters end 104 of the meter through an orifice 101 in flange 103 is conducted through manifold 150 to flow tube mounting block 120 having a surface 121. Within manifold 150 the material is divided and routed through flow tubes 130 and 130'. Upon exiting flow tubes 130 and 130', the process material is recombined in a single stream within manifold 150' and is thereafter routed to exit end 104' connected by flange 103' having bolt holes 102' to the process line (not shown).

Flow tubes 130 and 130' are selected and appropriately mounted to the flow tube mounting blocks 120 and 120' so as to have substantially the same mass distribution, moments of inertia and Young's modulus about bending axes W-W and W'-W', respectively. These bending axes go through brace bars 140 and 140'. Inasmuch as the Young's modulus of the flow tubes change with temperature, and this change affects the calculation of flow and density, resistive temperature detector (RTD) 190 is mounted to flow tube 130', to continuously measure the temperature of the flow tube. The temperature of the flow tube and hence the voltage appearing across the RTD for a given current passing therethrough is governed by the temperature of the material passing through the flow tube. The temperature dependent voltage appearing across the RTD is used in a well known method by meter electronics 20 to compensate for the change in elastic modulus of flow tubes 130 and 130' due to any changes in flow tube temperature. The RTD is connected to meter electronics 20 by lead 195.

Both flow tubes 130 and 130' are driven by driver 180 in opposite directions about their respective bending axes W and W' and at what is termed the first out-of-phase bending mode of the flow meter. This drive mechanism 180 may comprise any one of many well known arrangements, such as a magnet mounted to flow tube 130' and an opposing coil mounted to flow tube 130 and through which an alternating current is passed for vibrating both flow tubes. A suitable drive signal is applied by meter electronics 20, via lead 185, to drive mechanism 180.

Meter electronics 20 receives the RTD temperature signal on lead 195, and the left and right velocity signals appearing on leads 165L and 165R, respectively. Meter electronics 20 produces the drive signal appearing on lead 185 to drive element 180 and vibrate tubes 130 and 130'. Meter electronics 20 processes the left and right velocity signals and the RTD signal to compute the mass flow rate and the density of the material passing through meter assembly 10. This information, along with other information, is applied by meter electronics 20 over path 26 to utilization means 29.

Figure 2:
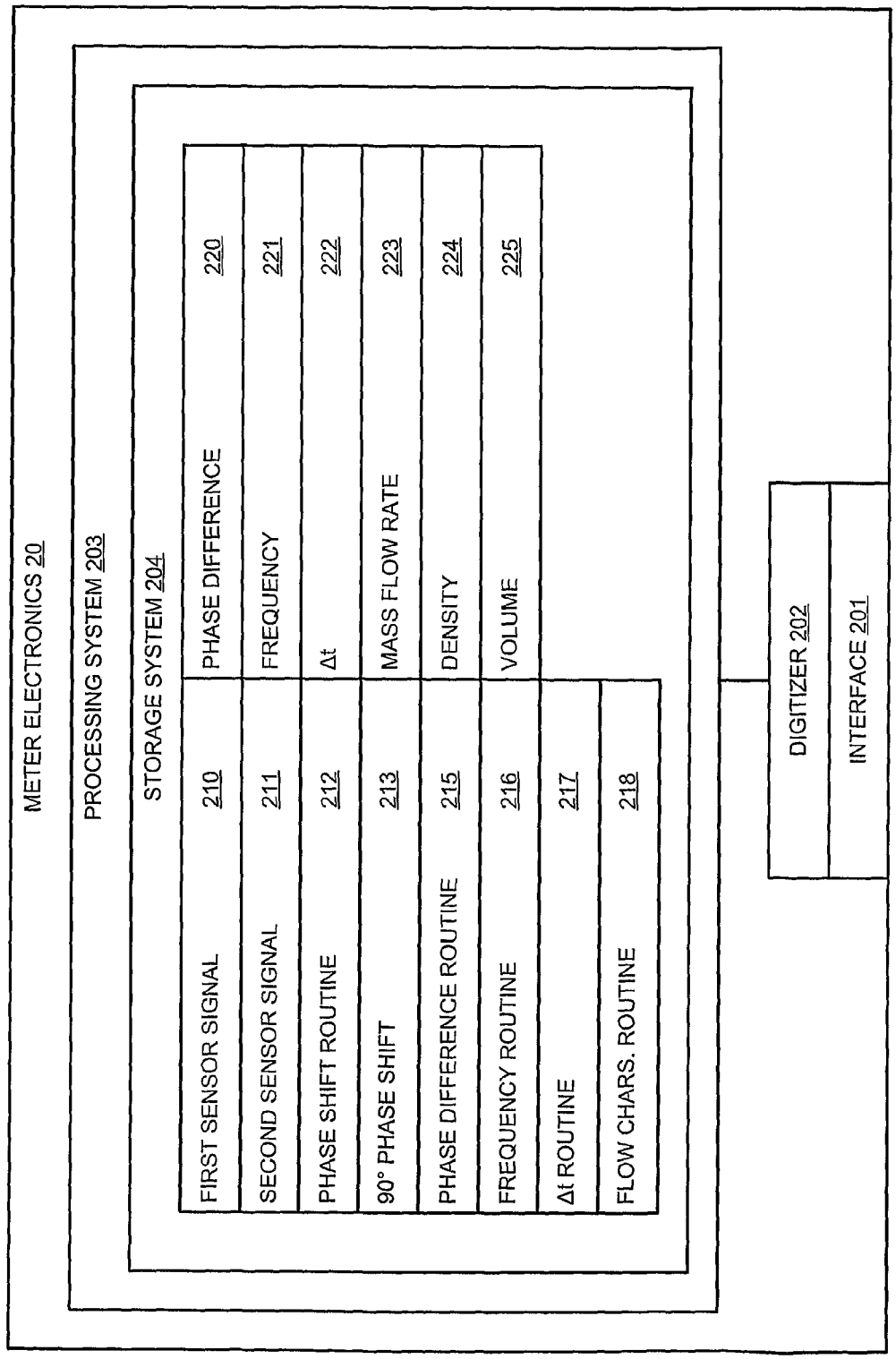
FIG. 2 shows meter electronics according to an embodiment of the invention.

FIG. 2 shows meter electronics 20 according to an embodiment of the invention. The meter electronics 20 can include an interface 201 and a processing system 203. The meter electronics 20 receives first and second sensor signals from the meter assembly 10, such as pickoff/velocity sensor signals. The meter electronics 20 can operate as a mass flow meter or can operate as a densitometer, including operating as a Coriolis flow meter. The meter electronics 20 processes the first and second sensor signals in order to obtain flow characteristics of the flow material flowing through the meter assembly 10. For example, the meter electronics 20 can determine one or more of a phase difference, a frequency, a time difference ($\Delta t$), a density, a mass flow rate, and a volume flow rate from the sensor signals, for example. In addition, other flow characteristics can be determined according to the invention. The determinations are discussed below.

The phase difference determination and the frequency determination are much faster and more accurate and reliable than such determinations in the prior art. In one embodiment, the phase difference determination and the frequency determination are directly derived from a phase shift of only one sensor signal, without the need for any frequency reference signal. This advantageously reduces the processing time required in order to compute the flow characteristics. In another embodiment, the phase difference is derived from phase shifts of both sensor signals, while the frequency is derived from only one phase shift signal. This increases the accuracy of both flow characteristics, and both can be determined much faster than in the prior art.

The prior art frequency determination methods typically take 1-2 seconds to perform. In contrast, the frequency determination according to the invention can be performed in as little as 50 milliseconds (ms). Even faster frequency determination is contemplated, depending on the type and configuration of the processing system, the sampling rate of the vibrational response, the filter sizes, the decimation rates, etc.

At the 50 ms frequency determination rate, the meter electronics 20 according to the invention can be about 40 times faster than the prior art.

The interface 201 receives the sensor signal from one of the velocity sensors 170L and 170R via the leads 100 of FIG. 1. The interface 201 can perform any necessary or desired signal conditioning, such as any manner of formatting, amplification, buffering, etc. Alternatively, some or all of the signal conditioning can be performed in the processing system 203.

In addition, the interface 201 can enable communications between the meter electronics 20 and external devices. The interface 201 can be capable of any manner of electronic, optical, or wireless communication.

The interface 201 in one embodiment is coupled with a digitizer 202, wherein the sensor signal comprises an analog sensor signal. The digitizer 202 samples and digitizes the analog sensor signal and produces a digital sensor signal. The digitizer 202 can also perform any needed decimation, wherein the digital sensor signal is decimated in order to reduce the amount of signal processing needed and to reduce the processing time. The decimation will be discussed in more detail below.

The processing system 203 conducts operations of the meter electronics 20 and processes flow measurements from the flow meter assembly 10. The processing system 203 executes one or more processing routines and thereby processes the flow measurements in order to produce one or more flow characteristics.

The processing system 203 can comprise a general purpose computer, a microprocessing system, a logic circuit, or some other general purpose or customized processing device. The processing system 203 can be distributed among multiple processing devices. The processing system 203 can include any manner of integral or independent electronic storage medium, such as the storage system 204.

The processing system 203 processes the sensor signal 210 in order to determine one or more flow characteristics from the sensor signal 210. The one or more flow characteristics can include a phase difference, a frequency, a time difference ($\Delta t$), a mass flow rate, and/or a density for the flow material, for example.

In the embodiment shown, the processing system 203 determines the flow characteristics from the two sensor signals 210 and 211 and the single sensor signal phase shift 213. The processing system 203 can determine at least the phase difference and the frequency from the two sensor signals 210 and 211 and the single phase shift 213. As a result, either a first or second phase shifted sensor signal (such as one of the upstream or downstream pickoff signals) can be processed by the processing system 203 according to the invention in order to determine a phase difference, a frequency, a time difference ($\Delta t$), and/or a mass flow rate for the flow material.

The storage system 204 can store flow meter parameters and data, software routines, constant values, and variable values. In one embodiment, the storage system 204 includes routines that are executed by the processing system 203. In one embodiment, the storage system 204 stores a phase shift routine 212, a phase difference routine 215, a frequency routine 216, a time difference ($\Delta t$) routine 217, and a flow characteristics routine 218.

In one embodiment, the storage system 204 stores variables used to operate a flowmeter, such as the Coriolis flow meter 5. The storage system 204 in one embodiment stores variables such as the first sensor signal 210 and the second sensor signal 211, which are received from the velocity/pickoff sensors 170L and 170R. In addition, the storage system 204 can store a 90 degree phase shift 213 that is generated in order to determine the flow characteristics.

In one embodiment, the storage system 204 stores one or more flow characteristics obtained from the flow measurements. The storage system 204 in one embodiment stores flow characteristics such as a phase difference 220, a frequency 221, a time difference ($\Delta t$) 222, a mass flow rate 223, a density 224, and a volume flow rate 225, all determined from the sensor signal 210.

The phase shift routine 212 performs a 90 degree phase shift on an input signal, i.e., on the sensor signal 210. The phase shift routine 212 in one embodiment implements a Hilbert transform (discussed below).

The phase difference routine 215 determines a phase difference using the single 90 degree phase shift 213. Additional information can also be used in order to compute the phase difference. The phase difference in one embodiment is computed from the first sensor signal 210, the second sensor signal 211, and the 90 degree phase shift 213. The determined phase difference can be stored in the phase difference 220 of the storage system 204. The phase difference, when determined from the 90 phase shift 213, can be calculated and obtained much faster than in the prior art. This can provide a critical difference in flow meter applications having high flow rates or where multi-phase flows occur. In addition, the phase difference can be determined independent of the frequency of either sensor signal 210 or 211. Moreover, because the phase difference is determined independently of the frequency, an error component in the phase difference does not include an error component of the frequency determination, i.e., there is no compounding error in the phase difference measurement. Consequently, the phase difference error is reduced over a phase difference of the prior art.

The frequency routine 216 determines a frequency (such as that exhibited by either the first sensor signal 210 or the second sensor signal 211) from the 90 degree phase shift 213. The determined frequency can be stored in the frequency 221 of the storage system 204. The frequency, when determined from the single 90 phase shift 213, can be calculated and obtained much faster than in the prior art. This can provide a critical difference in flow meter applications having high flow rates or where multi-phase flows occur.

The time difference ($\Delta t$) routine 217 determines a time difference ($\Delta t$) between the first sensor signal 210 and the second sensor signal 211. The time difference ($\Delta t$) can be stored in the time difference ($\Delta t$) 222 of the storage system 204. The time difference ($\Delta t$) comprises substantially the determined phase divided by the determined frequency, and is therefore used to determine the mass flow rate.

The flow characteristics routine 218 can determine one or more flow characteristics. The flow characteristics routine 218 can use the determined phase difference 220 and the determined frequency 221, for example, in order to accomplish these additional flow characteristics. It should be understood that additional information may be required for these determinations, such as the mass flow rate or density, for example. The flow characteristics routine 218 can determine a mass flow rate from the time difference ($\Delta t$) 222, and therefore from the phase difference 220 and the frequency 221. The formula for determining mass flow rate is given in U.S. Pat. No. 5,027,662 to Titlow et al., and is incorporated herein by reference. The mass flow rate is related to the mass flow of flow material in the meter assembly 10. Likewise, the flow characteristics routine 218 can also determine the density 224 and/or the volume flow rate 225. The determined mass flow rate, density, and volume flow rate can be stored in the mass flow rate 223, the density 224, and the volume 225 of the storage system 204, respectively. In addition, the flow characteristics can be transmitted to external devices by the meter electronics 20.

Figure 3:
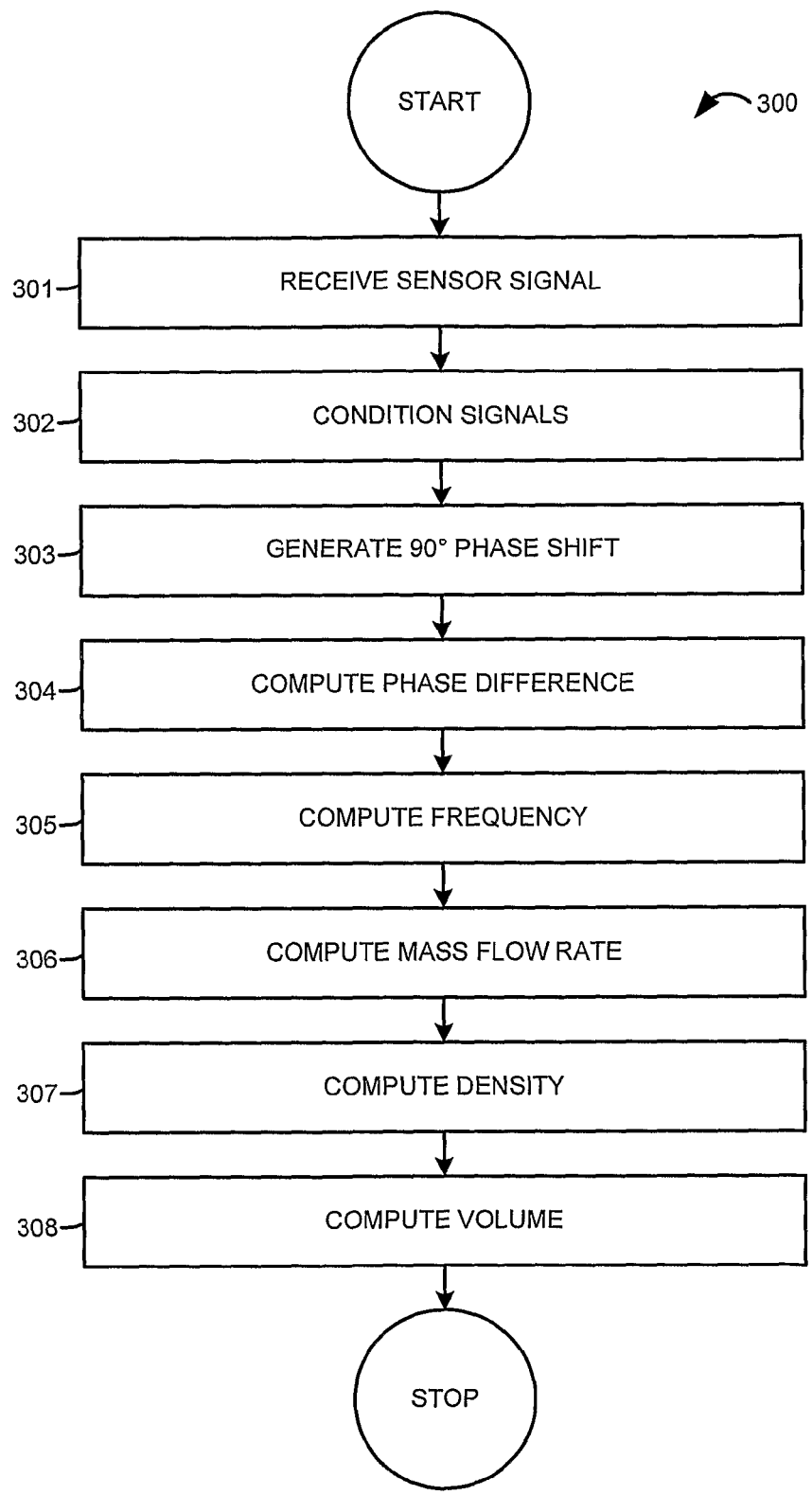
FIG. 3 is a flowchart of a method of processing a sensor signal in a flowmeter according to an embodiment of the invention.

FIG. 3 is a flowchart 300 of a method of processing sensor signals in a flowmeter according to an embodiment of the invention. In step 301, the first and second sensor signals are received. The first sensor signal can comprise either an upstream or downstream pickoff sensor signal.

In step 302, the sensor signals can be conditioned. In one embodiment, the conditioning can include filtering to remove noise and unwanted signals. In one embodiment, the filtering can comprise band-pass filtering centered around the expected fundamental frequency of the flow meter. In addition, other conditioning operations can be performed, such as amplification, buffering, etc. If the sensor signals comprise analog signals, the step can further comprise any manner of sampling, digitization, and decimation that are performed in order to produce digital sensor signals.

In step 303, a single 90 degree phase shift is generated. The 90 degree phase shift comprises a 90 degree phase shift of the sensor signal. The 90 degree phase shift can be performed by any manner of phase shift mechanism or operation. In one embodiment, the 90 degree phase shift is performed using a Hilbert transform, operating on digital sensor signals.

In step 304, a phase difference is computed, using the single 90 degree phase shift. Additional information can also be used in order to compute the phase difference. In one embodiment, the phase difference is determined from the first sensor signal, the second sensor signal, and the single 90 degree phase shift. The phase difference comprises a phase difference in the response signal, i.e., in a pickoff sensor, that is seen due to the Coriolis effect in the vibrating meter assembly 10.

The resulting phase difference is determined without the need for any frequency value in the calculation. The resulting phase difference can be obtained much faster than a phase difference calculated using a frequency. The resulting phase difference has a greater accuracy than a phase difference calculated using a frequency.

In step 305, a frequency is computed. The frequency according to the invention is advantageously computed from the 90 degree phase shift. The frequency in one embodiment uses the 90 degree phase shift and the corresponding sensor signal from which the 90 degree phase shift is derived. The frequency is a vibrational response frequency of one of the first sensor signal and the second sensor signal (the frequencies of the two sensor signals are substantially identical in operation). The frequency comprises a vibrational frequency response of the flowtube or flowtubes to a vibration generated by the driver 180.

The frequency thus derived is obtained without the need for any independent frequency reference signal. The frequency is obtained from the single 90 degree phase shift in an operation that is much faster than in the prior art. The resulting frequency has a greater accuracy than a frequency calculated in the prior art.

In step 306, a mass flow rate of flow material is computed. The mass flow rate is computed from the resulting phase difference and the resulting frequency computed in steps 304 and 305. In addition, the mass flow rate computation can compute a time difference ($\Delta t$) from the phase difference and the frequency, with the time difference ($\Delta t$) being ultimately used to compute the mass flow rate.

In step 307, the density can optionally be determined. The density can be determined as one of the flow characteristics, and can be determined from the frequency, for example.

In step 308, the volume flow rate can optionally be determined. The volume flow rate can be determined as one of the flow characteristics, and can be determined from the mass flow rate and the density, for example.

Figure 4:
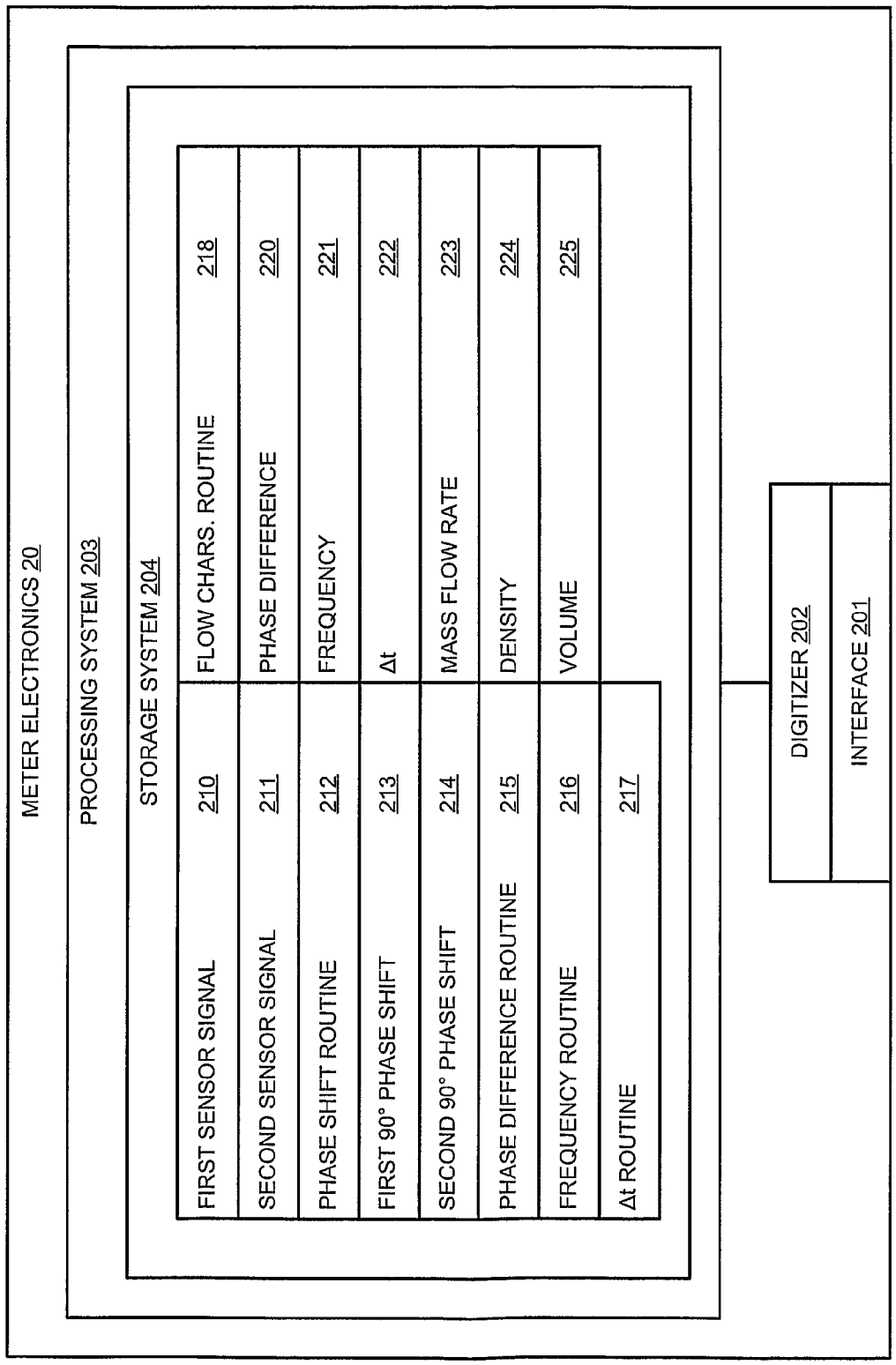
FIG. 4 shows the meter electronics according to an embodiment of the invention.

FIG. 4 shows the meter electronics 20 according to an embodiment of the invention. The elements in common with FIG. 2 share the same reference numbers.

The meter electronics 20 in this embodiment includes the first sensor signal 210 and the second sensor signal 211. The processing system 203 processes the first and second (digital) sensor signals 210 and 211 in order to determine one or more flow characteristics from the signals. As previously discussed, the one or more flow characteristics can include a phase difference, a frequency, a time difference ($\Delta t$), a mass flow rate, a density, and/or a volume flow rate for the flow material.

In the embodiment shown, the processing system 203 determines the flow characteristics from only the two sensor signals 210 and 211, without the need for any external frequency measurement and without the need for an external frequency reference signal. The processing system 203 can determine at least the phase difference and the frequency from the two sensor signals 210 and 211.

As was previously discussed, the storage system 204 stores a phase shift routine 212, a phase difference routine 215, a frequency routine 216, a time difference ($\Delta t$) routine 217, and a flow characteristics routine 218. The storage system 204 stores the first sensor signal 210 and the second sensor signal 211. The storage system 204 also stores a first 90 degree phase shift 213 and a second 90 degree phase shift that are generated from the sensor signals in order to determine the flow characteristics. As was previously discussed, the storage system 204 stores the phase difference 220, the frequency 221, the time difference ($\Delta t$) 222, the mass flow rate 223, the density 224, and the volume flow rate 225.

The phase shift routine 212 performs a 90 degree phase shift on an input signal, including on the first sensor signal 210 and on the second sensor signal 211. The phase shift routine 212 in one embodiment implements a Hilbert transform (discussed below).

The phase difference routine 215 determines a phase difference using the first 90 degree phase shift 213 and the second 90 degree phase shift 214. Additional information can also be used in order to compute the phase difference. The phase difference in one embodiment is computed from the first sensor signal 210, the second sensor signal 211, the first 90 degree phase shift 212, and the second 90 degree phase shift 213. The determined phase difference can be stored in the phase difference 220 of the storage system 204, as previously discussed. The phase difference, when determined using the first and second 90 phase shifts, can be calculated and obtained much faster than in the prior art. This can provide a critical difference in flow meter applications having high flow rates or where multi-phase flows occur. In addition, the phase difference can be determined independent of the frequency of the sensor signals 210 and 211. Moreover, because the phase difference is determined independently of the frequency, an error component in the phase difference does not suffer from an error component of the frequency determination, i.e., there is no compounding error in the phase difference measurement. Consequently, the phase difference error is reduced over a phase difference of the prior art.

The frequency routine 216 determines a frequency (such as that exhibited by either the first sensor signal 210 or the second sensor signal 211) from the first 90 degree phase shift 213 and the second 90 degree phase shift 214. The determined frequency can be stored in the frequency 221 of the storage system 204, as previously discussed. The frequency, when determined from the first and second 90 phase shifts, can be calculated and obtained much faster than in the prior art. This can provide a critical difference in flow meter applications having high flow rates or where multi-phase flows occur.

The time difference ($\Delta t$) routine 217 determines a time difference ($\Delta t$) between the first sensor signal 210 and the second sensor signal 211. The time difference ($\Delta t$) can be stored in the time difference ($\Delta t$) 222 of the storage system 204, as previously discussed. The time difference ($\Delta t$) comprises substantially the determined phase divided by the determined frequency, and is therefore used to determine the mass flow rate.

The flow characteristics routine 218 can determine one or more of the mass flow rate, the density, and/or the volume flow rate, as previously discussed.

Figure 5:
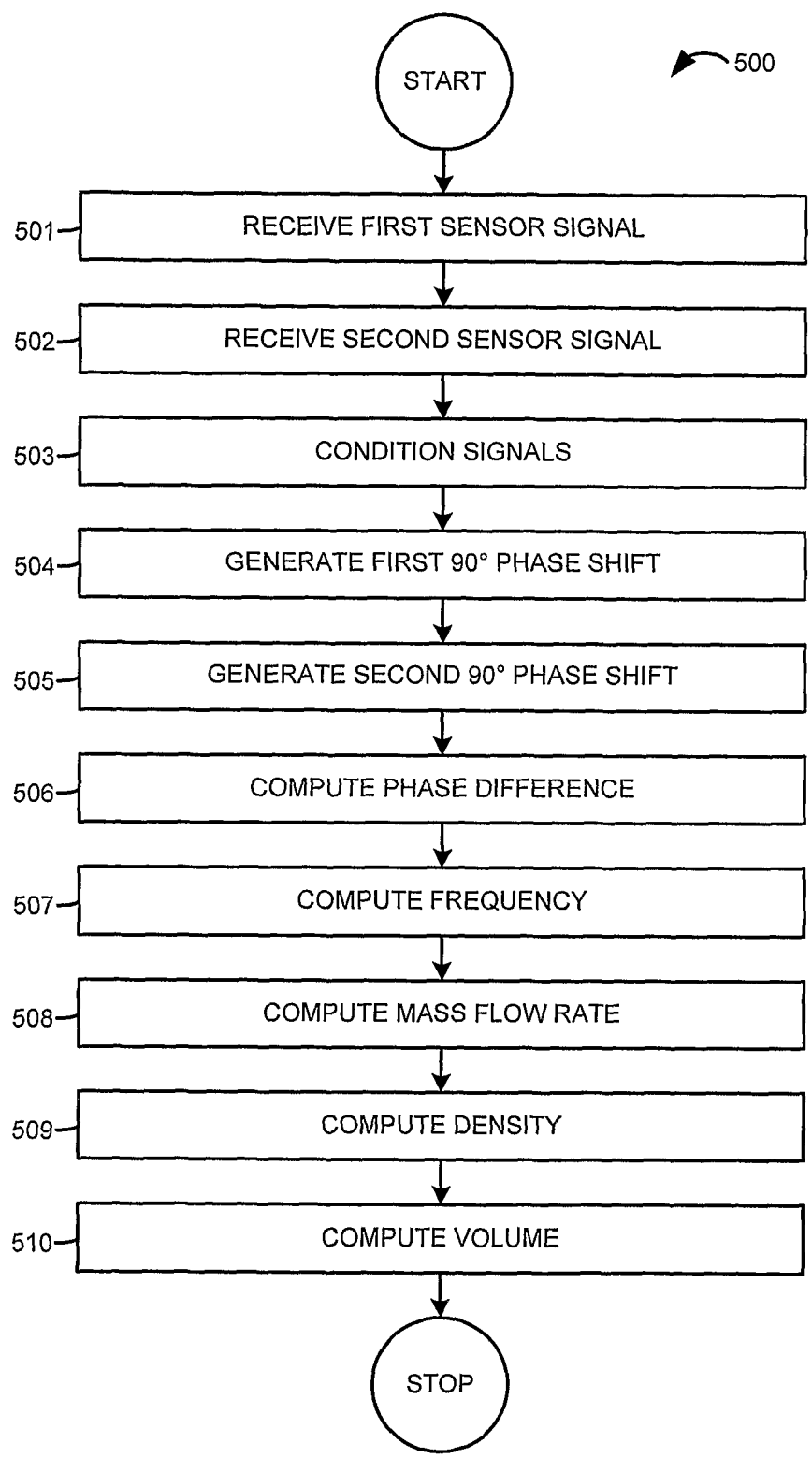
FIG. 5 is a flowchart of a method of processing first and second sensor signals in a flowmeter according to an embodiment of the invention.

FIG. 5 is a flowchart 500 of a method of processing first and second sensor signals in a flowmeter according to an embodiment of the invention. In step 501, the first sensor signal is received. In one embodiment, the first sensor signal comprises either an upstream or downstream pickoff sensor signal.

In step 502, the second sensor signal is received. In one embodiment, the second sensor signal comprises either a downstream or upstream pickoff sensor signal (i.e., the opposite of the first sensor signal).

In step 503, the sensor signals can be conditioned. In one embodiment, the conditioning can include filtering to remove noise and unwanted signals. In one embodiment, the filtering can comprise band-pass filtering, as previously discussed. In addition, other conditioning operations can be performed, such as amplification, buffering, etc. If the sensor signals comprise analog signals, the step can further comprise any manner of sampling, digitization, and decimation that are performed in order to produce digital sensor signals.

In step 504, a first 90 degree phase shift is generated. The first 90 degree phase shift comprises a 90 degree phase shift of the first sensor signal. The 90 degree phase shift can be performed by any manner of mechanism or operation. In one embodiment, the 90 degree phase shift is performed using a Hilbert transform, operating on digital sensor signals.

In step 505, a second 90 degree phase shift is generated. The second 90 degree phase shift comprises a 90 degree phase shift of the second sensor signal. As in the first 90 degree phase shift, the 90 degree phase shift can be performed by any manner of mechanism or operation.

In step 506, a phase difference is computed between the first sensor signal and the second sensor signal, using the first 90 degree phase shift and the second 90 degree phase shift. Additional information can also be used in order to compute the phase difference. In one embodiment, the phase difference is determined from the first sensor signal, the second sensor signal, the first 90 degree phase shift, and the second 90 degree phase shift. The phase difference comprises a phase difference in the response signal, i.e., in the two pickoff sensors, that is seen due to the Coriolis effect in the vibrating meter assembly 10.

The resulting phase difference is determined without the need for any frequency value in the calculation. The resulting phase difference can be obtained much faster than a phase difference calculated using a frequency. The resulting phase difference has a greater accuracy than a phase difference calculated using a frequency.

In step 507, a frequency is computed. The frequency according to the invention is advantageously computed from the first 90 degree phase shift and the second 90 degree phase shift. The frequency in one embodiment uses the 90 degree phase shift and the corresponding sensor signal from which the 90 degree phase shift is derived. The frequency is a vibrational response frequency of one of the first sensor signal and the second sensor signal (the frequencies of the two sensor signals are substantially identical in operation). The frequency comprises a vibrational frequency response of the flowtube or flowtubes to a vibration generated by the driver 180.

The frequency thus derived is obtained without the need for any independent frequency reference signal. The frequency is obtained from the 90 degree phase shifts in an operation that is much faster than in the prior art. The resulting frequency has a greater accuracy than a frequency calculated in the prior art.

In step 508, a mass flow rate of flow material is computed. The mass flow rate is computed from the resulting phase difference and the resulting frequency computed in steps 506 and 507. In addition, the mass flow rate computation can compute a time difference ($\Delta t$) from the phase difference and the frequency, with the time difference ($\Delta t$) being ultimately used to compute the mass flow rate.

In step 509, the density can optionally be determined, as previously discussed.

In step 510, the volume flow rate can optionally be determined, as previously discussed.

Figure 6:
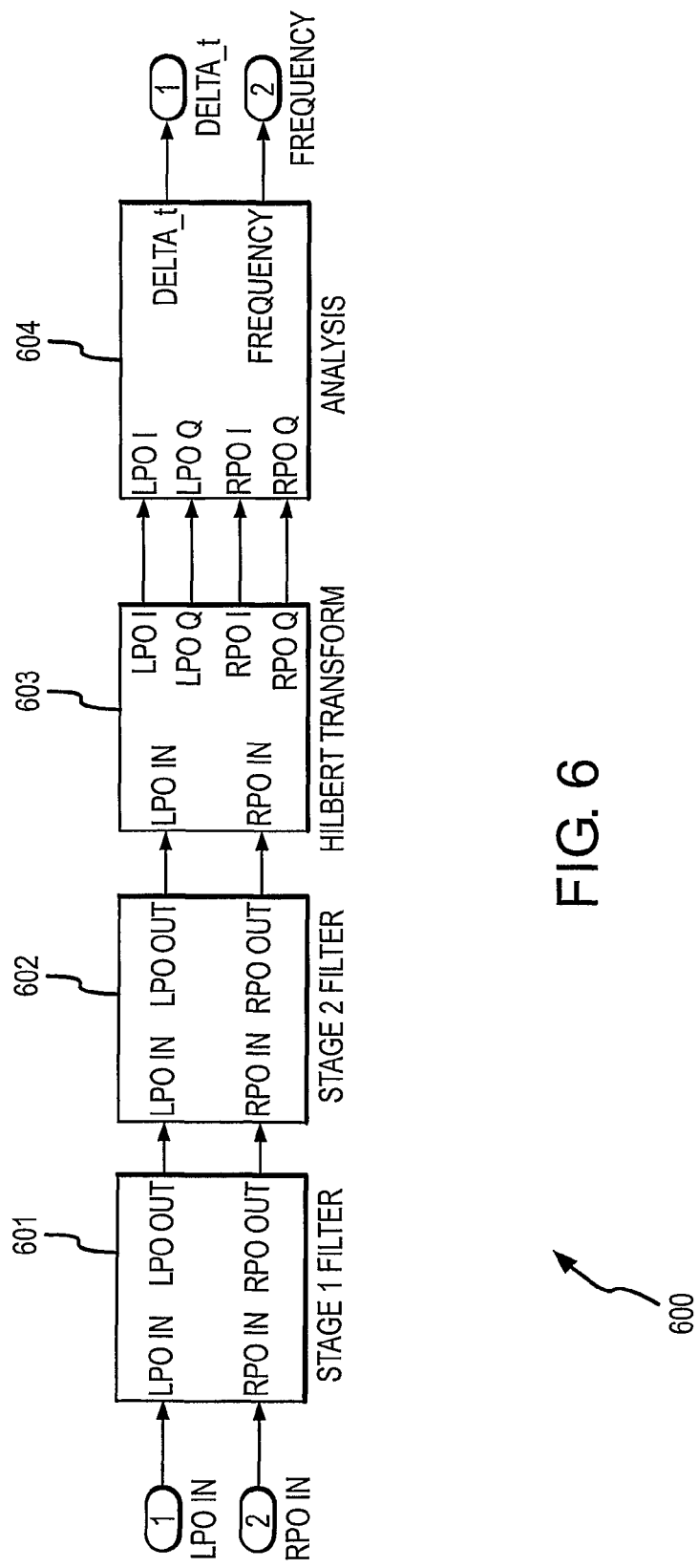
FIG. 6 is a block diagram of a portion of the processing system according to an embodiment of the invention.

FIG. 6 is a block diagram 600 of a portion of the processing system 203 according to an embodiment of the invention. In the figure, the blocks represent either processing circuitry or processing actions/routines. The block diagram 600 includes a stage 1 filter block 601, a stage 2 filter block 602, a Hilbert transform block 603, and an analysis block 604. The LPO and RPO inputs comprise the left pickoff signal input and the right pickoff signal input. Either the LPO or the RPO can comprise a first sensor signal.

In one embodiment, the stage 1 filter block 601 and the stage 2 filter block 602 comprise digital Finite Impulse Response (FIR) polyphase decimation filters, implemented in the processing system 203. These filters provide an optimal method for filtering and decimating one or both sensor signals, with the filtering and decimating being performed at the same chronological time and at the same decimation rate. Alternatively, the stage 1 filter block 601 and the stage 2 filter block 602 can comprise Infinite Impulse Response (IIR) filters or other suitable digital filters or filter processes. However, it should be understood that other filtering processes and/or filtering embodiments are contemplated and are within the scope of the description and claims.

Figure 7:
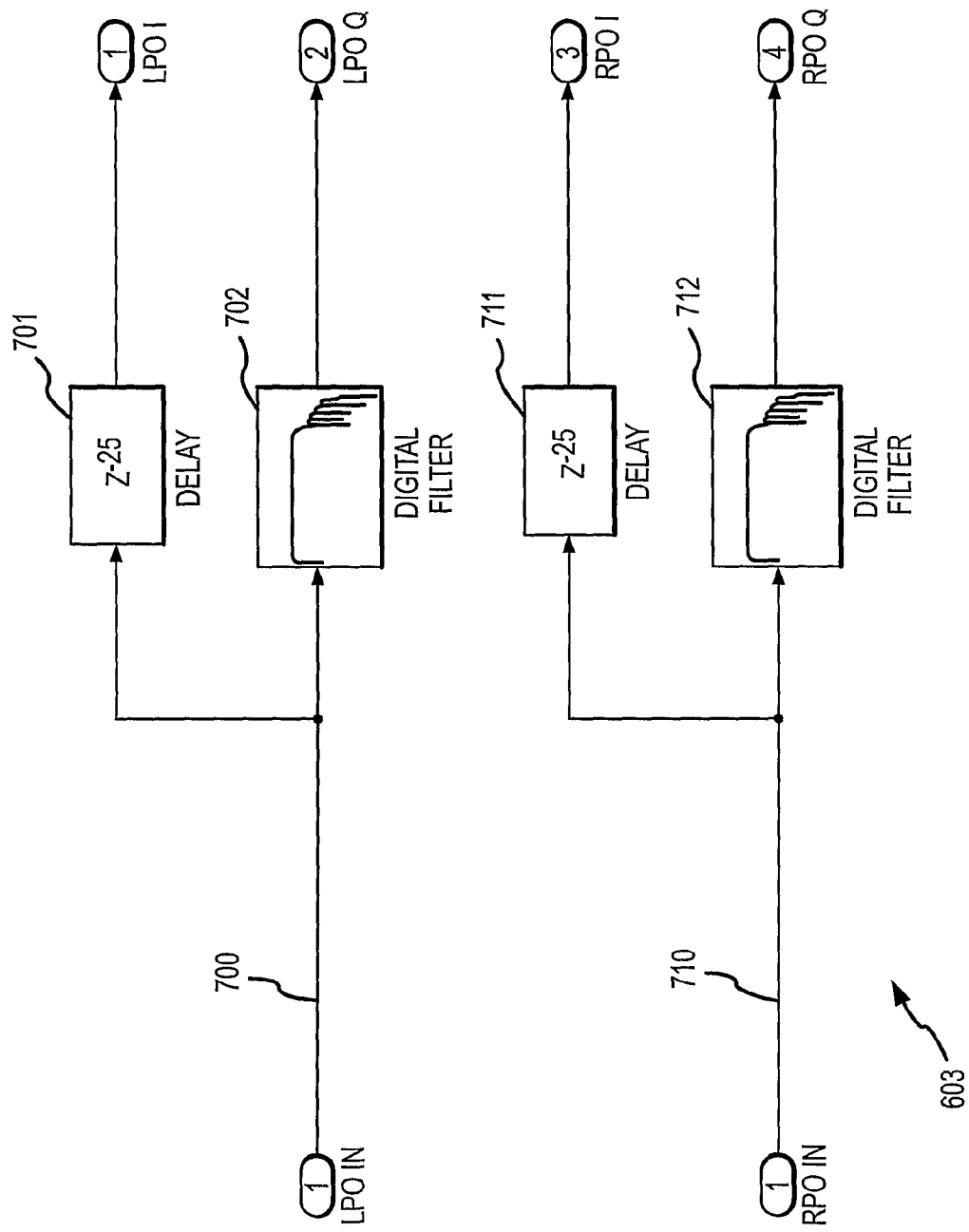
FIG. 7 shows detail of the Hilbert transform block according to an embodiment of the invention.

FIG. 7 shows detail of the Hilbert transform block 603 according to an embodiment of the invention. In the embodiment shown, the Hilbert transform block 603 includes a LPO branch 700 and a RPO branch 710. The LPO branch 700 includes a LPO delay block 701 in parallel with a LPO filter block 702. Likewise, the RPO branch includes an RPO delay block 711 in parallel with an RPO filter block 712. The LPO delay block 701 and the RPO delay block 711 introduce sampling delays. The LPO delay block 701 and the RPO delay block 711 therefore select LPO and RPO digital signal samples that are chronologically later in time that the LPO and RPO digital signal samples that are filtered by the LPO filter block 702 and the RPO filter block 712. The LPO filter block 702 and the RPO filter block 712 perform a 90 degree phase shift on the inputted digital signal samples.

The Hilbert transform block 603 is a first step to providing the phase measurement. The Hilbert transform block 603 receives the filtered, decimated LPO and RPO signals and performs a Hilbert transform. The Hilbert transform produces 90 degree phase-shifted versions of the LPO and RPO signals, i.e., it produces quadrature (Q) components of the original, in-phase (I) signal components. The output of the Hilbert transform block 603 therefore provides the new quadrature (Q) components LPO Q and RPO Q, along with the original, in-phase (I) signal components LPO I and RPO I.

The inputs to the Hilbert transform block 603 can be represented as:

$$LPO = A_{lpo} \cos(\omega t) \tag{2}$$

$$RPO = A_{rpo} \cos(\omega t + \emptyset) \tag{3}$$

Using the Hilbert transform the output becomes:

$$LPO_{hilbert} = A_{lpo} \sin(\omega t) \tag{4}$$

$$RPO_{hilbert} = A_{rpo} \sin(\omega t + \phi)] \tag{5}$$

Combining the original terms with the output of the Hilbert transform yields:

$$LPO = A_{lpo}[\cos(\omega t) + i \sin(\omega t)] = A_{lpo} e^{j(\omega t)} \tag{6}$$

$$RPO = A_{rpo}[\cos(\omega t + \phi) + i \sin(\omega t + \phi)] = A_{rpo} e^{j(\omega t + \phi)} \tag{7}$$

Figure 8:
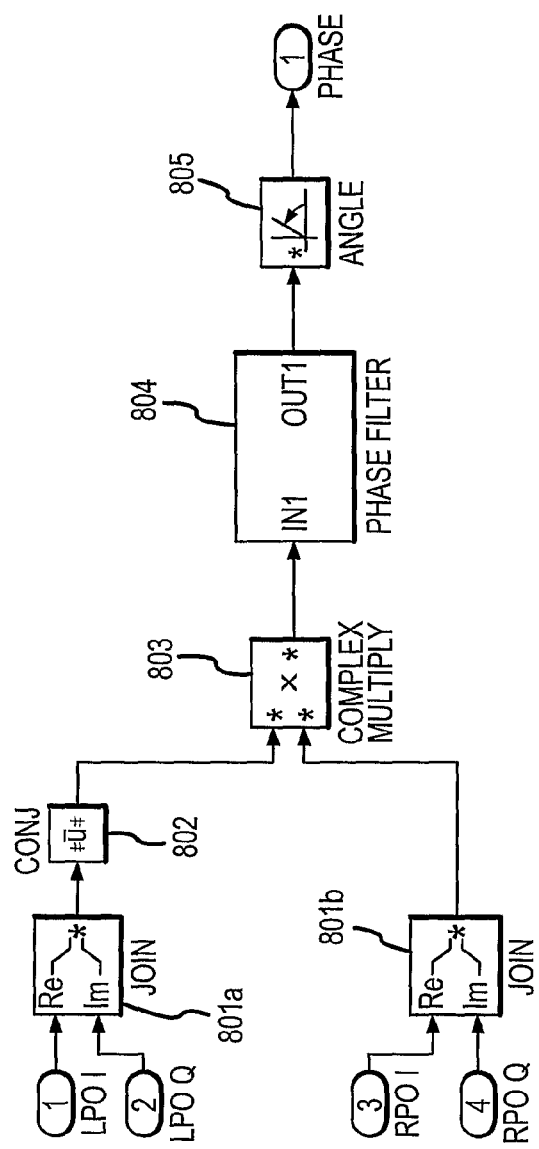
FIGS. 8 and 9 are block diagrams of two independent branches of the analysis block according to an embodiment of the invention.
Figure 9:
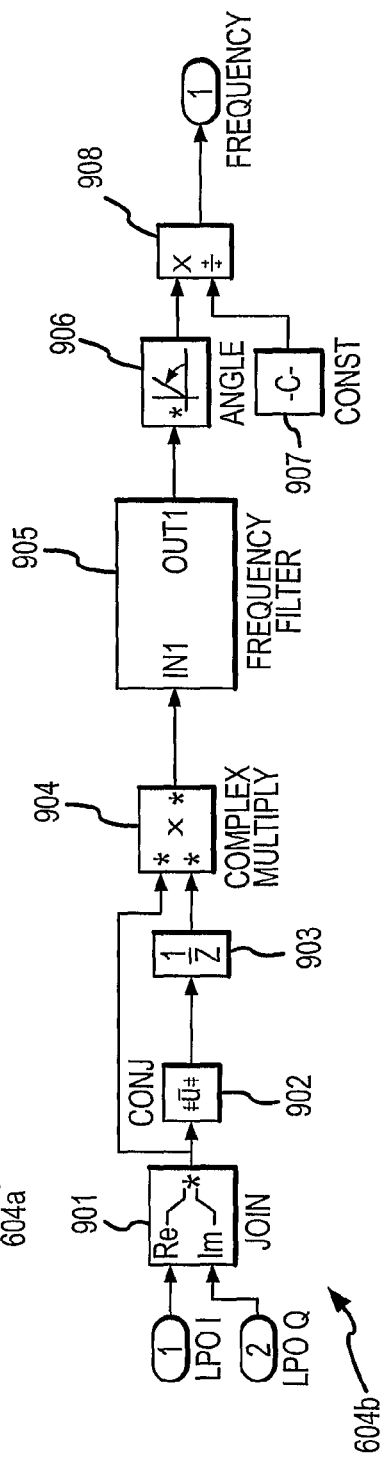

FIGS. 8 and 9 are block diagrams of two independent branches of the analysis block 604 according to an embodiment of the invention. The analysis block 604 is the final stage of the frequency, differential phase, and delta T ($\Delta t$) measurement. FIG. 8 is phase portion 604a comprising a first branch that determines a phase difference from the in-phase (I) and quadrature (Q) components. FIG. 9 is a frequency portion 604b that determines a frequency from the in-phase (I) and quadrature (Q) components of a single sensor signal. The single sensor signal can comprise the LPO signal, as shown, or can alternatively comprise the RPO signal.

In the embodiment of FIG. 8, the phase portion 604a of the analysis block 604 includes join blocks 801a and 801b, a conjugate block 802, a complex multiplication block 803, a filter block 804, and a phase angle block 805.

The join blocks 801a and 801b receive both in-phase (I) and quadrature (Q) components of a sensor signal and pass them on. The conjugate block 802 performs a complex conjugate on a sensor signal (here the LPO signal), and forms a negative of the imaginary signal. The complex multiplication block 803 multiplies the RPO signal and the LPO signal, implementing equation (8) below. The filter block 804 implements a digital filter, such as the FIR filter discussed above. The filter block 804 can comprise a polyphase decimation filter that is used to remove harmonic content from the in-phase (I) and quadrature (Q) components of the sensor signal, as well as to decimate the signal. The filter coefficients can be chosen to provide decimation of the inputted signal, such as decimation by a factor of 10, for example. The phase angle block 805 determines the phase angle from the in-phase (I) and quadrature (Q) components of the LPO signal and the RPO signal. The phase angle block 805 implements equation (11) shown below.

The phase portion 604a shown in FIG. 8 implements the following equation:

$$\overline{LPO} \times RPO = A_{lpo} e^{-j(\omega t)} \times A_{Rpo} e^{j(\omega t + \phi)} = A_{lpo} \times A_{Rpo} e^{j(-\omega t + \omega t + \phi)} \tag{8}$$

where $\overline{LPO}$ is the complex conjugate of LPO. Assuming that:

$$A_{Rpo} = A_{Lpo} = A \tag{9}$$

then:

$$\overline{LPO} \times RPO = A^2 e^{j(\phi)} = A^2 [\cos(\phi) + i \sin(\phi)] \tag{10}$$

The resulting differential phase angle is:

$$\phi = \tan^{-1}\left[\frac{\sin(\phi)}{\cos(\phi)}\right] \quad (11)$$

FIG. 9 is a block diagram of a frequency portion 604b of the analysis block 604 according to the invention. The frequency portion 604b can operate on either the left or right pickoff signal (LPO or RPO). The frequency portion 604b in the embodiment shown includes a join block 901, a complex conjugate block 902, a sampling block 903, a complex multiplication block 904, a filter block 905, a phase angle block 906, a constant block 907, and a division block 908.

As previously discussed, the join block 901 receives both in-phase (I) and quadrature (Q) components of a sensor signal and passes them on. The conjugate block 902 performs a complex conjugate on a sensor signal, here the LPO signal, and forms a negative of the imaginary signal. The delay block 903 introduces a sampling delay into the frequency portion 604b, and therefore selects a digital signal sample that is chronologically older in time. This older digital signal sample is multiplied with the current digital signal in the complex multiplication block 904. The complex multiplication block 904 multiplies the LPO signal and the LPO conjugate signal, implementing equation (12) below. The filter block 905 implements a digital filter, such as the FIR filter previously discussed The filter block 905 can comprise a polyphase decimation filter that is used to remove harmonic content from the in-phase (I) and quadrature (Q) components of the sensor signal, as well as to decimate the signal. The filter coefficients can be chosen to provide decimation of the inputted signal, such as decimation by a factor of 10, for example. The phase angle block 906 determines a phase angle from the in-phase (I) and quadrature (Q) components of the LPO signal. The phase angle block 906 implements a portion of equation (13) below. The constant block 907 supplies a factor comprising a sample rate $F_s$ divided by two pi, as shown in equation (14). The division block 908 performs the division operation of equation (14).

The frequency portion 604b implements the following equation:

$$\overline{LPO}_{(n-1)} \times LPO_{(n)} = A_{lpo}e^{-j(\omega t-1)} \times A_{lpo}e^{j(\omega t)} = A^2_{lpo}e^{j(\omega t-\omega t-1)} \quad (12)$$

The angle between two consecutive samples is therefore:

$$\omega t - \omega t_{-1} = \tan^{-1}\left[\frac{\sin(\omega t - \omega t_{-1})}{\cos(\omega t - \omega t_{-1})}\right] \quad (13)$$

which is the radian frequency of the left pick-off. Converting to Hz:

$$f_{lpo} = \frac{(\omega t - \omega t_{-1}) \times Fs}{2\pi} \quad (14)$$

where "Fs" is the rate of the Hilbert transform block 603. In the example previously discussed, "Fs" is about 2 kHz.

Figure 10:
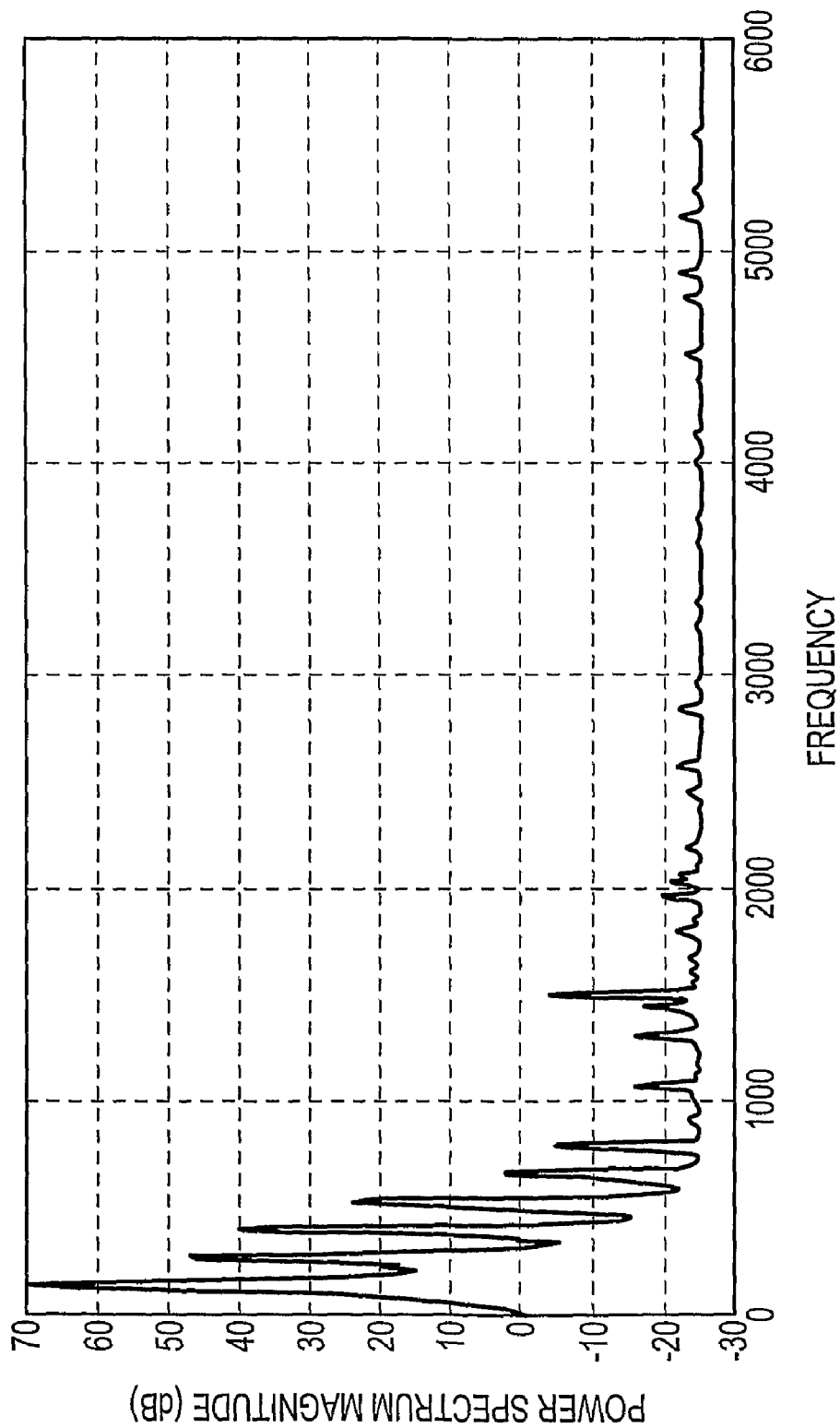
FIG. 10 is a power spectrum density plot of a pick-off sensor signal of a flow meter under normal conditions.

FIG. 10 is a power spectrum density plot of a pick-off sensor signal of a flow meter under normal conditions. The fundamental frequency of the flowmeter is the tallest spike of the graph and is located at about 135 Hz. The figure also shows several other large spikes in the frequency spectrum (the first non-fundamental mode is the twist mode at a frequency of about 1.5 times the frequency of the fundamental mode). These spikes comprise harmonic frequencies of the flowmeter and also comprise other, undesirable sensor modes (i.e., a twist mode, a second bend mode, etc.).

Figure 11:
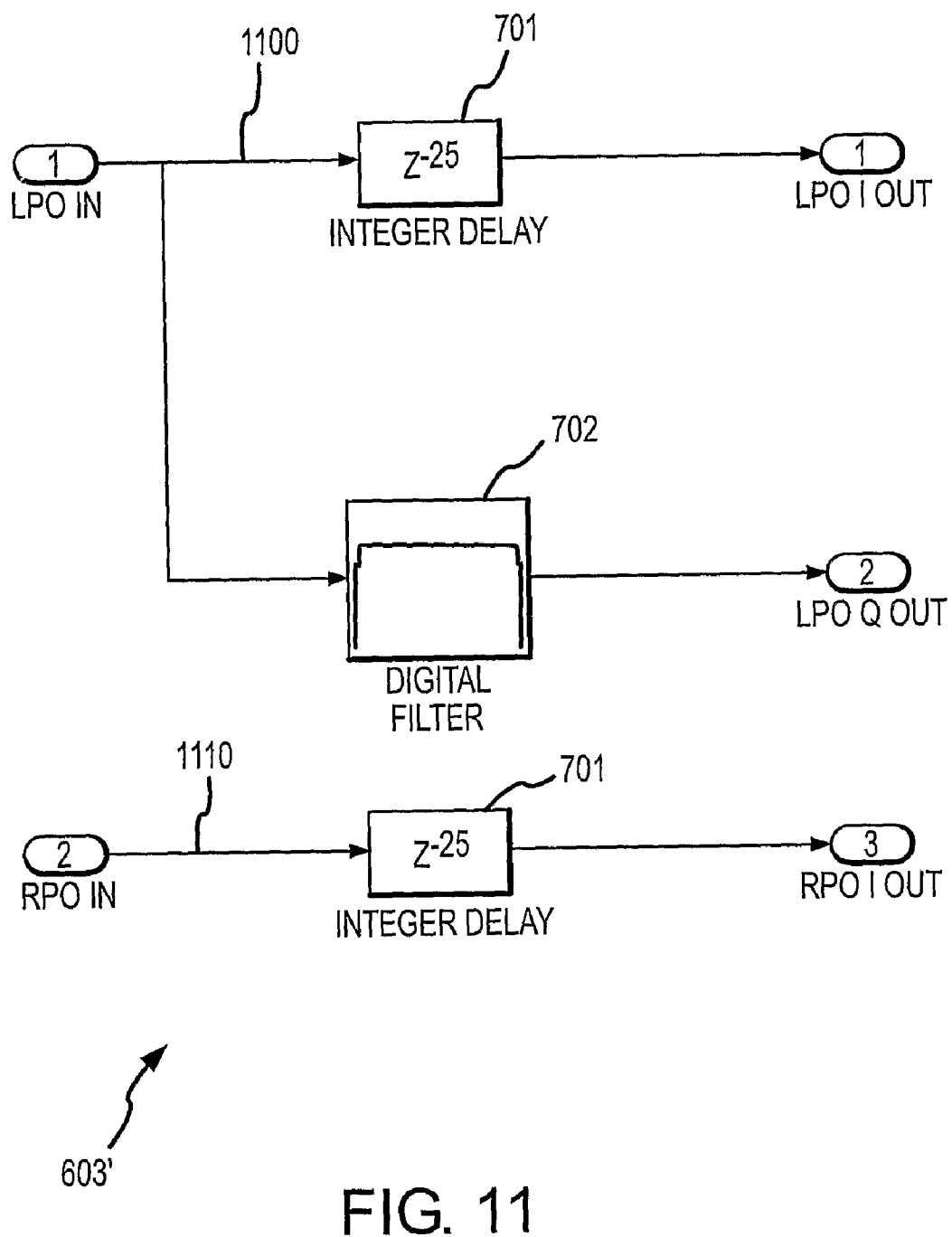
FIG. 11 shows a Hilbert transform block according to the single phase shift embodiment.

FIG. 11 shows an alternative Hilbert transform block 603' according to a single phase shift embodiment. The Hilbert transform block 603' in this embodiment includes a LPO branch 1100 and a RPO branch 1110. The LPO branch 1100 includes a delay block 701 in parallel with a filter block 702. The RPO branch 1110 in this embodiment includes only a delay block 701. As before, the delay blocks 701 introduce sampling delays. As before, the filter block 702 performs a 90 degree phase shift on the inputted digital signal sample. It should be understood that alternatively the Hilbert transform block 603' could phase shift just the RPO signal.

This processing embodiment uses the Hilbert transform/phase shift of only one sensor signal in order to derive both the frequency and the phase difference (see FIGS. 2-3). This significantly reduces the number of computations needed to perform a phase measurement and significantly reduces the number of computations needed to obtain the mass flow rate.

In this embodiment, the output of the Hilbert transform block 603' will provide the quadrature (Q) component of either the left or right sensor signal, but not both. In the example below, the LPO signal is phase shifted.

$$LPO = A_{lpo}\cos(\omega t) \quad (26)$$

$$RPO = A_{rpo}\cos(\omega t + \phi) \quad (27)$$

Using the Hilbert transform, the output becomes:

$$LPO_{hilbert} = A_{lpo}\sin(\omega t) \quad (28)$$

$$RPO = A_{rpo}\cos(\omega t + \phi) \quad (29)$$

Combining the LPO original term with the output of the Hilbert transform (i.e., with the 90 phase shift) yields:

$$LPO = A_{lpo}[\cos(\omega t) + i\sin(\omega t)] = A_{lpo}e^{j(\omega t)} \quad (30)$$

while the RPO stays the same:

$$RPO = A_{rpo}\cos(\omega t + \phi) \quad (31)$$

$$= A_{rpo}\left[\frac{e^{j(\omega t+\phi)} + e^{-j(\omega t+\phi)}}{2}\right]$$

Figure 12:
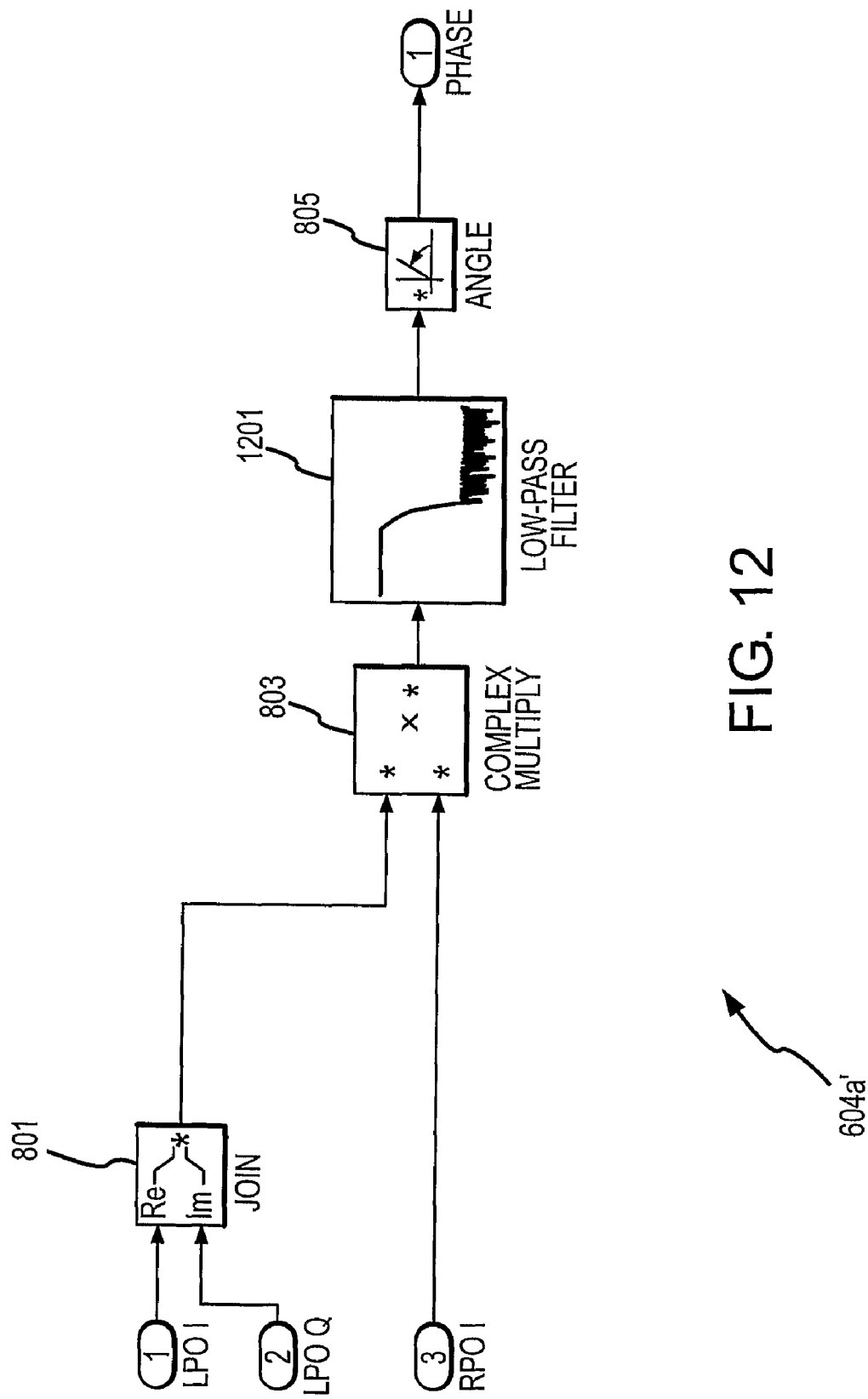
FIG. 12 shows the analysis block for the single phase shift embodiment.

FIG. 12 shows the analysis block 604a' for the single phase shift embodiment. The analysis block 604a' in this embodiment includes one join block 801, the complex multiplication block 803, a low-pass filter block 1201, and a phase angle block 805. The analysis block 604a' in this embodiment implements the following equation:

$$LPO \times RPO = A_{lpo}e^{-j(\omega t)} \times A_{rpo}\left[\frac{e^{j(\omega t+\phi)} + e^{-j(\omega t+\phi)}}{2}\right] \quad (32)$$

$$= \frac{A_{lpo} \times A_{Rpo}}{2}[e^{j(-\omega t+\omega t+\phi)} + e^{j(\omega t+\omega t+\phi)}]$$

The low-pass filter block 1201 comprises a low-pass filter that removes a high-frequency component produced by the complex multiplication block 803. The low-pass filter block 1201 can implement any manner of low-pass filtering operation. The result of the multiplication operation produces two terms. The ($-\omega t + \omega t + \emptyset$) term combines and simplifies to a phase-only $\emptyset$ term (a DC result), since the ($-\omega t$) and the ($\omega t$) terms cancel each other out. The ($\omega t + \omega t + \emptyset$) simplifies to a (2ωt+Ø) term, at twice the frequency. Since the result is the sum of 2 terms, the high frequency (2ωt+Ø) term can be removed. The only signal of interest here is the DC term. The high frequency (2ωt+Ø) term can be filtered out of the result using a low-pass filter. The cut-off of the low-pass filter can be located anywhere between zero and 2ω.

After filtering, the result is:

$$LPO \times RPO = A^2 e^{j(\phi)} \qquad (33)$$
$$= \frac{A^2}{2}[\cos(\phi) + i\sin(\phi)]$$

Therefore, the differential phase angle is:

$$\phi = \tan^{-1}\left[\frac{\sin(\phi)}{\cos(\phi)}\right] \qquad (34)$$

By taking the Hilbert transform of one pick-off signal instead of two, the computational load needed to perform phase and frequency estimation in Coriolis mass flow meters is advantageously reduced. The phase and frequency can therefore be determined using two sensor signals, but using only one 90 degree phase shift.

Figure 13:
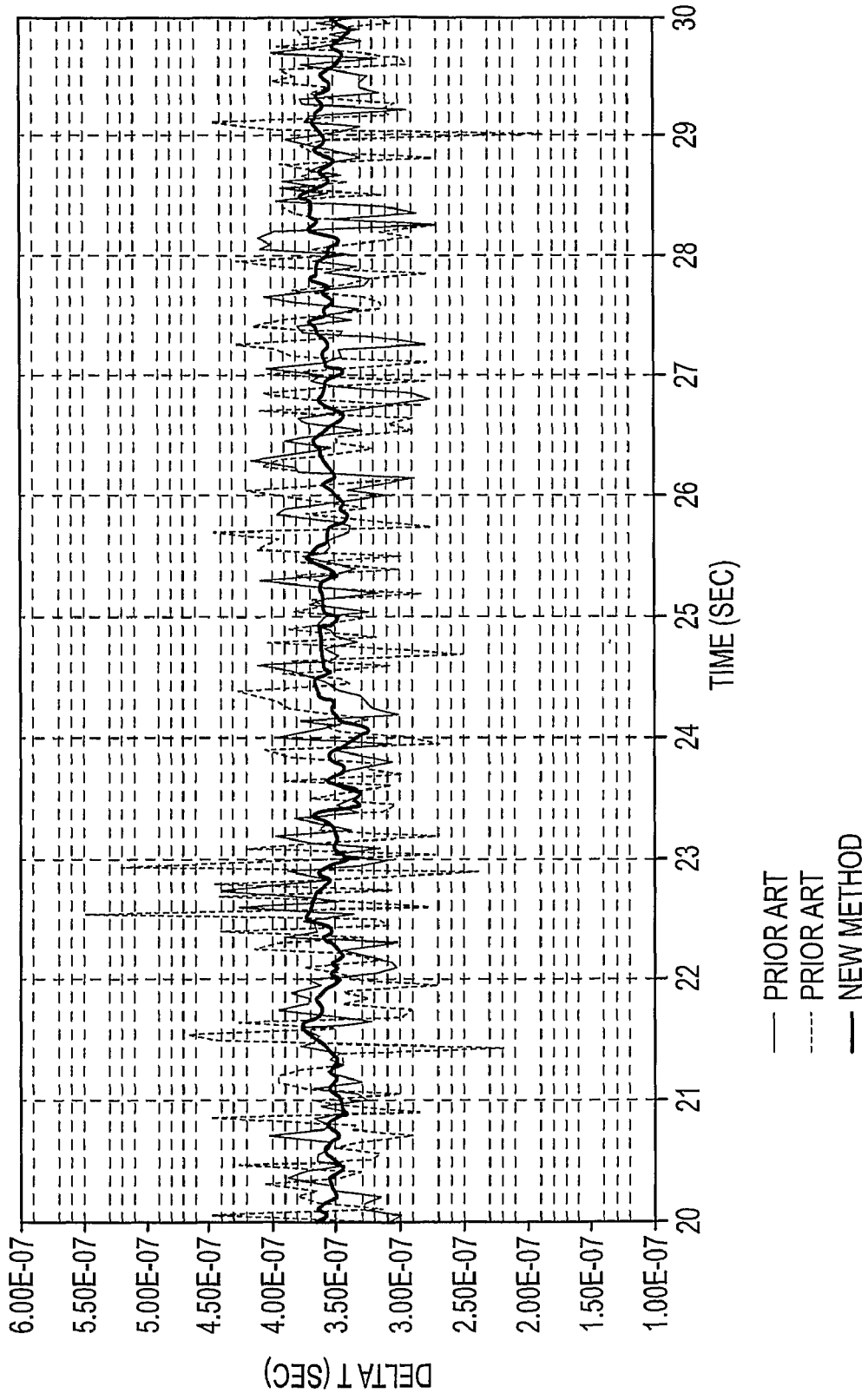
FIG. 13 shows the sensor processing of the invention as compared to the prior art, wherein a time difference (Δt) value of each is compared.

FIG. 13 shows the sensor processing of the invention as compared to the prior art, wherein a time difference (Δt) value of each is compared. The chart shows a flow material including a gas flow (i.e., gas bubbles, for example). Under this condition, the flow noise is substantially reduced in the new algorithm because of the rate of phase and frequency calculation. It can be seen from the graph that the result derived by the invention does not display the large peaks and valleys that are reflected in prior art (Δt) measurements.

Figure 14:
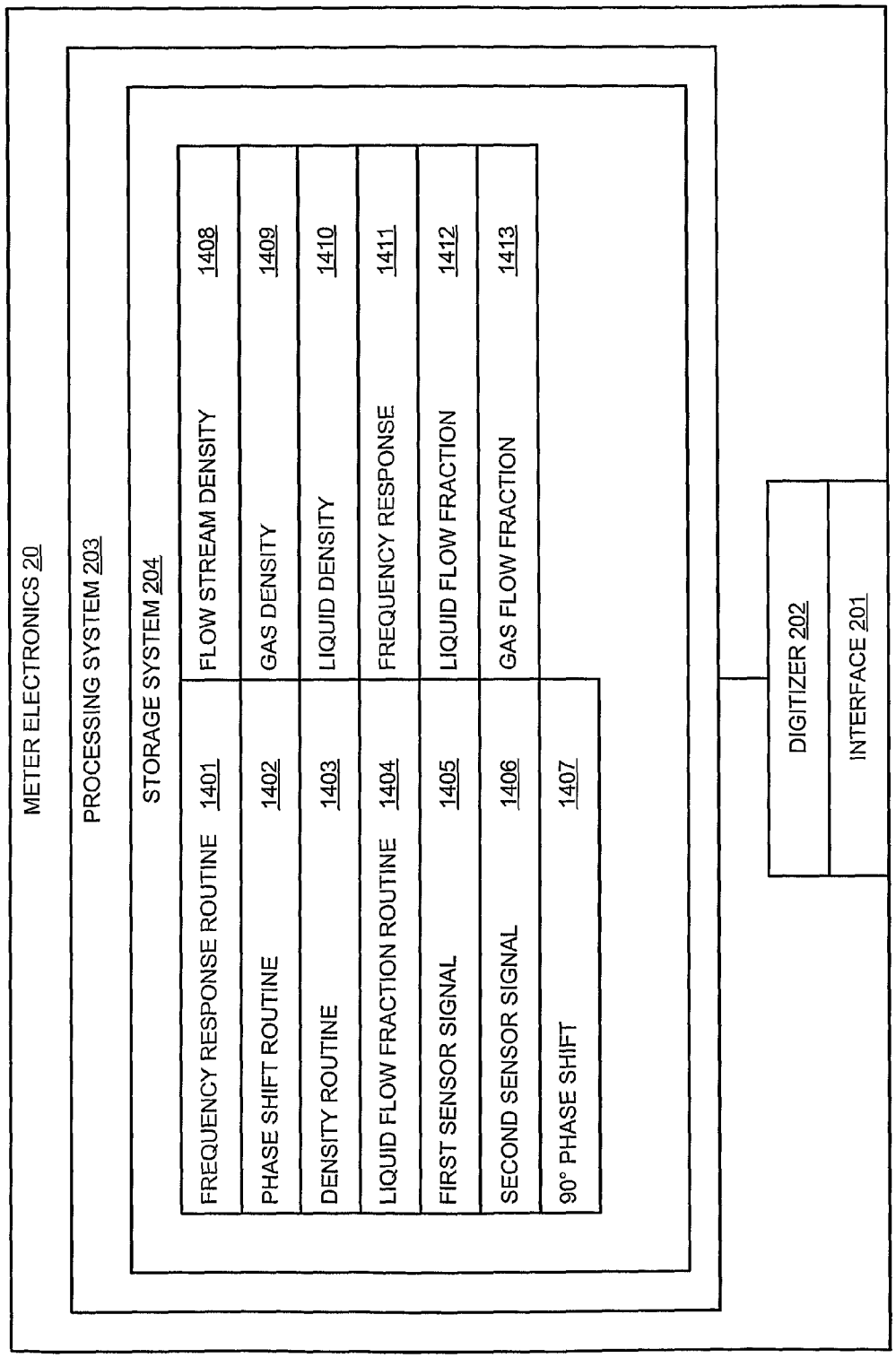
FIG. 14 shows the meter electronics according to another embodiment of the invention.

FIG. 14 shows the meter electronics 20 according to an embodiment of the invention. The meter electronics 20 of this embodiment can include the interface 201, the digitizer 202, the processing system 203, and the storage system 204, as previously discussed. It should be understood that the meter electronics 20 of this figure can include various other components and/or routines (such as those previously discussed). Components and/or routines in common with other embodiments share common reference numbers.

In operation, the meter electronics 20 receives and processes a first sensor signal 1405 and a second sensor signal 1406 from the flow meter. The first sensor signal 1405 and the second sensor signal 1406 comprise time-varying electronic signals that are substantially continuously received and processed by the meter electronics 20, such as signals from the pick-off sensors 170L and 170R. The meter electronics 20 can process the first sensor signal 1405 and the second sensor signal 1406 in order to obtain the frequency response 1411 and ultimately the liquid flow fraction 1412. Using the liquid flow fraction 1412, then the gas flow fraction 1413 can also be easily determined.

The processing system 203 can be configured to receive the first and second sensor signals 1405 and 1406 from the interface 201, determine a flow stream density 1408 of the gas flow material using the first sensor signal 1405 and the second sensor signal 1406, compare the flow stream density 1408 to at least one of a gas density 1409 that is representative of a gas flow fraction of the gas flow material and to a liquid density 1410 that is representative of a liquid flow fraction, and determine the liquid flow fraction 1412 from the flow stream density 1408 and at least one of the gas density 1409 and the liquid density 1410. In some embodiments, the flow stream density 1408 is compared to both the gas density 1409 and the liquid density 1410. In addition, the processing system 203 can be configured to receive the first and second sensor signals 1405 and 1406 from the interface 201, generate a 90 degree phase shift 1407 from the first sensor signal 1405, compute a frequency response 1411 using the 90 degree phase shift 1407 and the first sensor signal 1405, determine a flow stream density 1408 of the gas flow material using the frequency response 1411, and determine the liquid flow fraction 1412 from the flow stream density 1408.

In addition to the liquid flow fraction and the gas flow fraction, the meter electronics 20 can process the first sensor signal 1405 and the second sensor signal 1406 in order to obtain one or more other flow characteristics. The one or more other flow characteristics can include, for example, a phase difference or time delay between sensor signals, a mass flow rate, a volume flow rate, etc. Other flow characteristics are contemplated and are within the scope of the description and claims.

The gas flow material can comprise any gas or gas mixture. One type of gas flow material comprises a gas derived from a well. For example, the gas flow material can comprise natural gas. However, other gases or gas mixtures are contemplated and are within the scope of the description and claims.

The liquid flow fraction can include any liquid entrained in the gas flow material. A liquid flow fraction can comprise a liquid stream, a liquid vapor, or liquid drops. For example, the liquid can comprise water in a natural gas flow. Alternatively, the liquid can comprise glycol in a natural gas flow, such as a glycol carryover from a drying process. In another alternative, the liquid can comprise oil in the gas flow material, such as oil introduced into the gas flow material by pumps, regulators, or other flow handling mechanisms. However, other liquids or liquid combinations are contemplated and are within the scope of the description and claims.

The meter electronics 20 of this embodiment can store and execute processing routines. The processing routines in one embodiment include a density routine 1403, a liquid flow fraction routine 1404, a phase shift routine 1402, and a frequency response routine 1401. It should be understood that the processing system 203 can include other routines, such as the routines that were previously discussed.

The meter electronics 20 can include variables and working values. The variables and working values in one embodiment include a first sensor signal 1405, a second sensor signal 1406, a 90 degree phase shift 1407, a flow stream density 1408, a gas density 1409, a liquid density 1410, a frequency response 1411, a liquid flow fraction 1412, and an optional gas flow fraction 1413. It should be understood that the processing system 203 can operate on or produce other variables, such as the variables that were previously discussed.

The frequency of the meter assembly 10 will change when a liquid flow fraction passes through the meter assembly 10. The frequency will decrease as the liquid flow fraction increases, in contrast to a pure gas flow. This is due to the increased density when a liquid flow fraction is present. Therefore, the flow stream density can be used to determine the liquid flow fraction.

The frequency response routine 1401 receives the first sensor signal 1405 and the second sensor signal 1406. As previously discussed, the first and second sensor signals 1405 and 1406 reflect the response of the one or more flow conduits to a drive vibration imposed on the flow assembly 10. The frequency response routine 1401 processes at least the first sensor signal 1405 in order to compute the frequency response 1411. As was previously discussed, the first sensor signal 1405 can comprise the electronic signal received from either pick-off sensor. The frequency response 1411 is inherently related to the flow of gas flow material through the flow meter, and therefore varies with the density of the gas flow material in the flow meter. For example, entrained liquid passing through the flow meter will cause the frequency to decrease, as the density in the flow meter increases and as the vibrational response is temporarily more damped by flow material. The frequency response 1411 can be computed by using the first sensor signal 1405 and the 90 degree phase shift 1407, as previously discussed. Therefore, by employing the fast frequency (and flow stream density determinations), the meter electronics 20 can determine the liquid flow fraction 1412, and can substantially instantaneously determine the liquid flow fraction 1412.

The phase shift routine 1402 processes the first sensor signal 1405 in order to phase shift the first sensor signal 1405 and produce the 90 degree phase shift 1407, as previously discussed. The phase shift routine 1402 can be executed by the frequency response routine 1401. Alternatively, the phase shift routine 1402 can be integrated into the frequency response routine 1401.

The density routine 1403 determines the flow stream density 1408 from the first sensor signal 1405 and the second sensor signal 1406. In one embodiment, the density routine 1403 uses the frequency response 1411 in the flow stream density determination. The flow stream density 1408 is related to the density of the gas flow material, and varies according to the liquid flow fraction in the gas flow material.

The liquid flow fraction routine 1404 uses the flow stream density 1408 to produce the liquid flow fraction 1412. The liquid flow fraction 1412 is related to the amount (or percentage) of liquid in the gas flow material. The determination is discussed below in conjunction with FIG. 15. In addition, the liquid flow fraction routine 1404 can also produce the gas flow fraction 1413, wherein the gas flow fraction 1413 is related to the amount/percentage of gas in the gas flow material.

The first sensor signal 1405 and the second sensor signal 1406 store vibrational responses received from the meter assembly 10. The first sensor signal 1405 and the second sensor signal 1406 can comprise digital representations of an analog electrical signal received from the meter assembly 10. The first sensor signal 1405 and the second sensor signal 1406 can comprise sampled portions of the electrical signal.

The gas density 1409 can store a (known) gas density that is representative of a gas flow fraction of the gas flow material (i.e., a density of a pure gas without a liquid flow fraction). The gas density 1409 is used in a comparison with the determined flow stream density in order to determine the liquid flow fraction. The comparison is discussed below in conjunction with FIG. 15.

The liquid density 1410 can store a predetermined liquid density that is representative of the liquid density of a pure liquid. The liquid density 1409 can also be used in a comparison to the flow stream density and for the liquid flow fraction determination.

The frequency, when determined using the phase shift methods previously described, can be quickly obtained, in contrast to the prior art. Moreover, the frequency can be determined substantially instantaneously. The instantaneous frequency determination is advantageously available for use in other determinations, such as in determining a flow stream density and determining a liquid flow fraction according to the invention. Because the frequency can be substantially instantaneously determined, the liquid flow fraction can be quickly and accurately determined for the gas flow material.

It should be understood that the meter electronics 20 can iteratively receive and process the sensor signals. As a result, the meter electronics 20 can continuously and substantially instantaneously determined a liquid fraction in the gas flow material. The meter electronics 20 can substantially continuously perform the liquid flow fraction determination process over time as various levels of liquid flow fraction pass through the flow meter.

Figure 15:
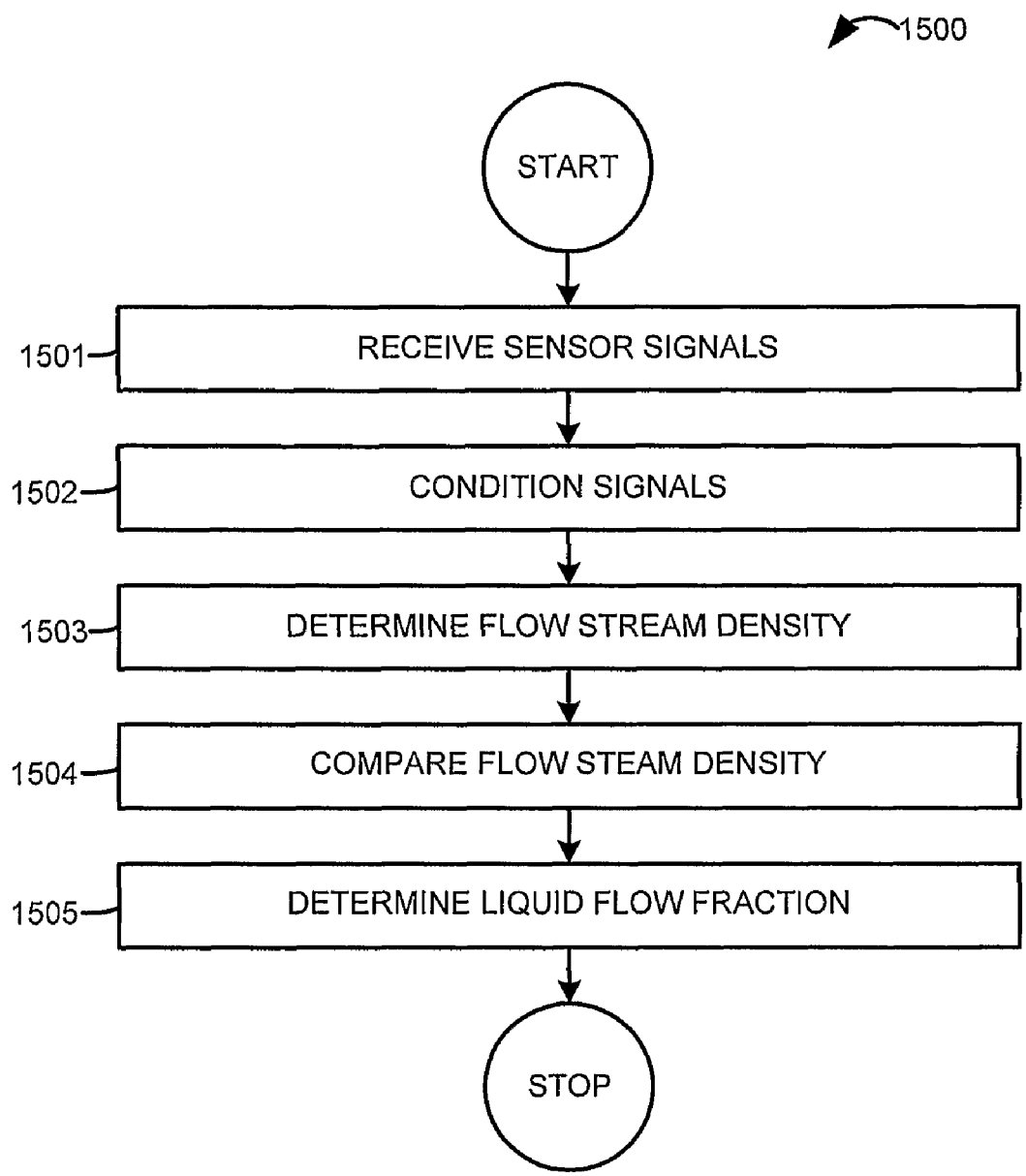
FIG. 15 is a flowchart of a method for determining a liquid flow fraction in a gas flow material flowing through a flow meter according to an embodiment of the invention.

FIG. 15 is a flowchart 1500 of a method for determining a liquid flow fraction in a gas flow material flowing through a flow meter according to an embodiment of the invention. In step 1501, first and second sensor signals are received from the meter assembly 10, as previously discussed.

In step 1502, the sensor signals can be conditioned, as previously discussed.

In step 1503, a flow stream density of the gas flow material is determined. The flow stream density is determined using the first sensor signal and the second sensor signal. Other flow characteristics, variables, and/or constants can also be used in making the determination, if needed.

In step 1504, the flow stream density is compared to a gas density and to a liquid density. The gas density is representative of a gas flow fraction of the gas flow stream and the liquid density is representative of the liquid flow fraction. In one embodiment, both densities are known and used. In another embodiment, only one of the two densities is known and used.

Figure 16:
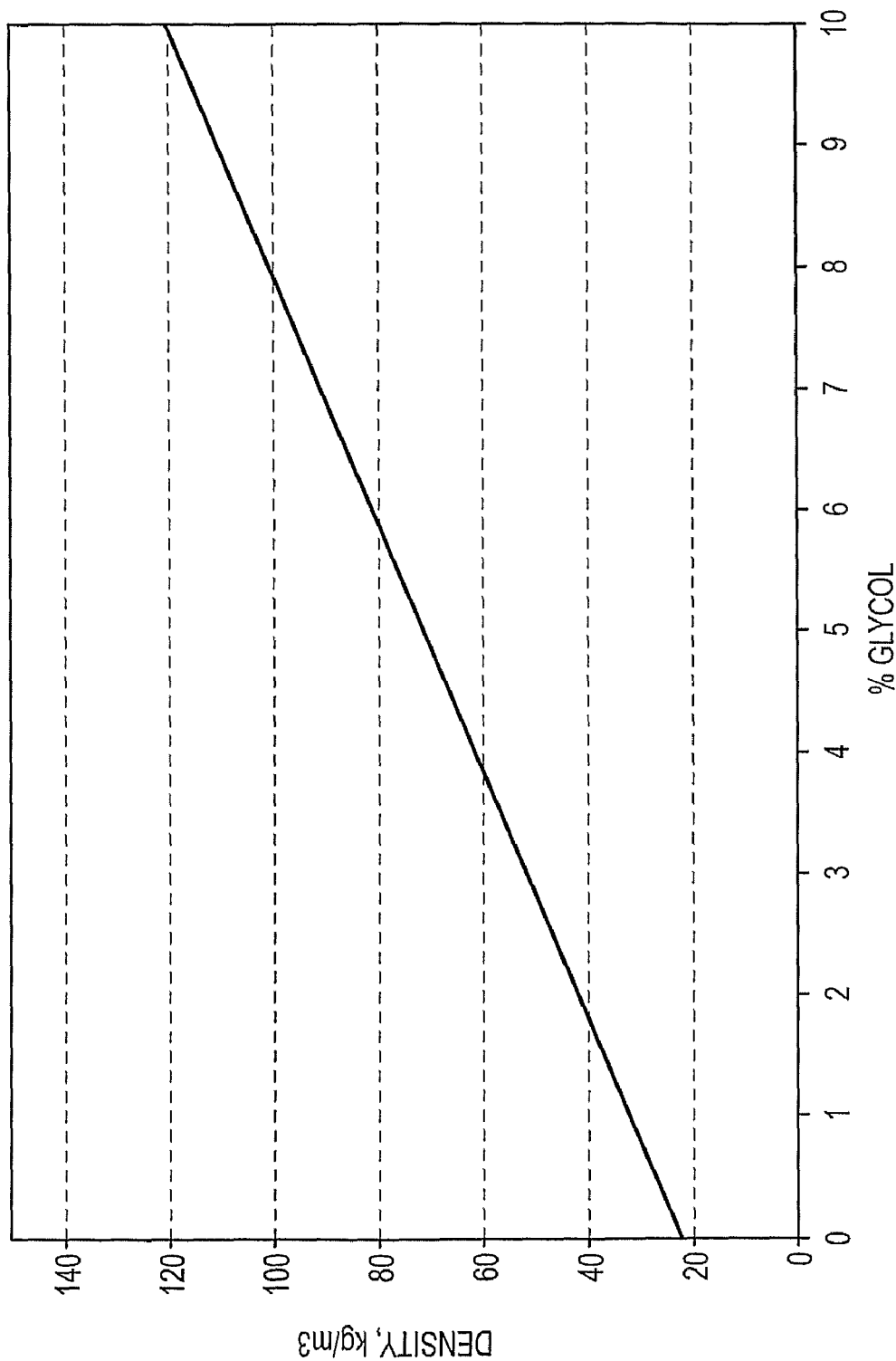
FIG. 16 is a graph of a natural gas density versus glycol percentage (i.e., liquid flow fraction).

FIG. 16 is a graph of natural gas density versus glycol percentage (i.e., liquid flow fraction). The table represents a set of data that is used for the comparison. However, any type of data structure can be used, and the data does not have to be in a table form. The diagonal graph line represents a gas flow material density for various fractions of gas versus glycol. It can be seen from the graph that the overall gas flow material density is proportional to the liquid flow fraction. Therefore, using at least the measured gas flow material (i.e., total) density and a known gas density, the liquid flow fraction can be determined. It should be understood that the data lookup can include other factors, such as pressure and temperature, for example. It should be understood that although the graph is for natural gas and glycol, other gases and liquids can be used and determined.

Referring again to FIG. 15, in step 1505 the liquid flow fraction is determined. The liquid flow fraction comprises the quantity or percentage of liquid in the gas flow material. The liquid flow fraction can be subsequently used for performing other computations, such as a gas mass flow rate and/or a liquid mass flow rate, for example. The liquid flow fraction can be determined from the comparison of the flow stream density to at least the known gas density. Alternatively, the comparison can comprise a comparison of the flow stream density to both the known gas density and the known liquid density.

By comparing the flow stream density to the known gas density and the known liquid density, a ratio can be formed that can be used for the liquid flow fraction determination. The ratio comprises:

$$D_{measured} = X(D_G)/D_L \tag{35}$$

where $D_{measured}$ is the flow stream density as determined from the sensor signals, $D_G$ is the know gas density, $D_L$ is the known liquid density, and X is the liquid flow fraction. Consequently, the liquid flow fraction X can be determined as:

$$X = D_{measured}(D_L)/D_G \tag{36}$$

Figure 17:
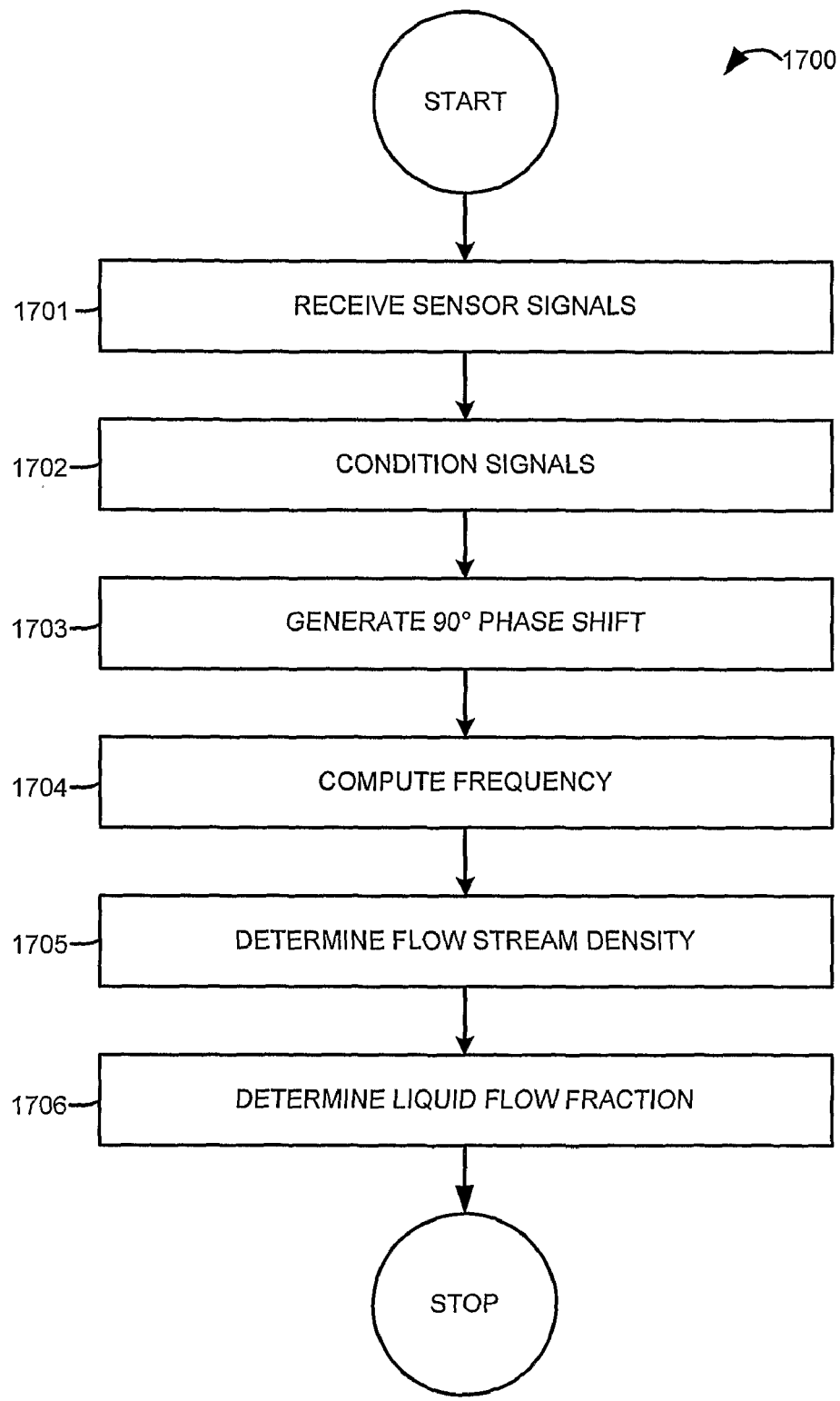
FIG. 17 is a flowchart of a method for determining a liquid flow fraction in a gas flow material flowing through a flow meter according to an embodiment of the invention.

FIG. 17 is a flowchart 1700 of a method for determining a liquid flow fraction in a gas flow material flowing through a flow meter according to an embodiment of the invention. In step 1701, first and second sensor signals are received from the meter assembly 10, as previously discussed.

In step 1702, the sensor signals can be conditioned, as previously discussed.

In step 1703, a 90 degree phase shift is generated from the first sensor signal. The 90 degree phase shift can be generated as previously discussed. Although the first sensor signal is phase shifted as an example, it should be understood that either sensor signal can be used.

In step 1704, a frequency response of the meter assembly 10 is computed. The frequency response can be computed using the 90 degree phase shift and the first sensor signal, as previously discussed.

In step 1705, a flow stream density of the gas flow material is determined using the frequency response. In one embodiment, the flow stream density is determined by squaring the frequency response and inverting the squared frequency response (since density=$1/f^2$). It should be understood that other flow characteristics, variables, and/or constants can also be used in making the determination, if needed.

In step 1706, the liquid flow fraction is determined. The liquid flow fraction can be determined from the comparison of the flow stream density to the known gas density, as previously discussed.

The meter electronics and method according to the invention can be employed according to any of the embodiments in order to provide several advantages, if desired. The invention can determine a liquid flow fraction in a gas flow material. The invention can determine a liquid flow fraction from a first sensor signal and a second sensor signal. The invention can determine a liquid flow fraction from a flow stream density. The invention can determine a liquid flow fraction using a frequency response. The invention can determine a liquid flow fraction using a first sensor signal and a 90 degree phase shift of the first sensor signal. The invention can also determine a gas flow fraction, along with the liquid flow fraction. The invention can set an alarm condition if the liquid flow fraction exceeds a liquid fraction threshold.

We claim:

1. Meter electronics (20) for determining a liquid flow fraction in a gas flow material flowing through a flow meter (5), the meter electronics (20) comprising:
   an interface (201) for receiving a first sensor signal and a second sensor signal from the flow meter (5); and
   a processing system (203) in communication with the interface (201) and configured to receive the first and second sensor signals from the interface (201), generate a 90 degree phase shift from the first sensor signal, compute a frequency response using the 90 degree phase shift and the first sensor signal, determine a substantially instantaneous flow stream density of the gas flow material using the frequency response, compare the substantially instantaneous flow stream density to one or both of a predetermined gas density that is representative of a gas flow fraction of the gas flow material and a predetermined liquid density that is representative of a liquid flow fraction, and determine the liquid flow fraction from the flow stream density and one or both of the predetermined gas density and the predetermined liquid density.

2. The meter electronics (20) of claim 1, with the processing system (203) being further configured to determine the gas flow fraction.

3. The meter electronics (20) of claim 1, with the processing system (203) being further configured to square the frequency response to generate a squared frequency response, and invert the squared frequency response to generate the substantially instantaneous flow stream density of the gas flow material.

4. The meter electronics (20) of claim 1, with the processing system (203) being further configured to compare the liquid flow fraction to a predetermined liquid fraction threshold and set an alarm condition if the liquid flow fraction exceeds the predetermined liquid fraction threshold.

5. The meter electronics (20) of claim 1, with the flow meter (5) comprising a Coriolis flow meter.

6. The meter electronics (20) of claim 1, with the flow meter (5) comprising a vibrating densitometer.

7. The meter electronics (20) of claim 1, with the comparing further comprising comparing the substantially instantaneous flow stream density to a drive gain and to at least one of a predetermined gas density that is representative of a gas flow fraction of the gas flow material and a predetermined liquid density that is representative of a liquid flow fraction.

8. Meter electronics (20) for determining a liquid flow fraction in a gas flow material flowing through a flow meter (5), the meter electronics, (20) comprising:
   an interface (201) for receiving a first sensor signal and a second sensor signal from the flow meter (5); and
   a processing system (203) in communication with the interface (201) and configured to receive the first and second sensor signals from the interface (201), generate a 90 degree phase shift from the first sensor signal, compute a frequency response using the 90 degree phase shift and the first sensor signal, determine a flow stream density of the gas flow material using the frequency response, and determine the liquid flow fraction from the flow stream density.

9. The meter electronics (20) of claim 8, with the processing system (203) being further configured to determine the gas flow fraction.

10. The meter electronics (20) of claim 8, with the processing system (203) being further configured to determine the flow stream density by squaring the frequency response to generate a squared frequency response and invert the squared frequency response to generate the flow stream density.

11. The meter electronics (20) of claim 8, with the processing system (203) being further configured to determine a flow stream density of the gas flow material from the first sensor signal and the second sensor signal, compare the flow stream density to at least one of a predetermined gas density that is representative of a gas flow fraction of the gas flow material and a predetermined liquid density that is representative of a liquid flow fraction, and determine the liquid flow fraction from the comparison.

12. The meter electronics (20) of claim 8, with the processing system (203) being further configured to compare the liquid flow fraction to a predetermined liquid fraction threshold and set an alarm condition if the liquid flow fraction exceeds the predetermined liquid fraction threshold.

13. The meter electronics (20) of claim 8, with the flow meter (5) comprising a Coriolis flow meter.

14. The meter electronics (20) of claim 8, with the flow meter (5) comprising a vibrating densitometer.

15. The meter electronics (20) of claim 8, with the determining the liquid flow fraction further comprising determining the liquid flow fraction from the flow stream density and a drive gain.

16. A method for determining a liquid flow fraction in a gas flow material flowing through a flow meter, the method comprising:
   receiving a first sensor signal and a second sensor signal from the flowmeter;

generating a 90 degree phase shift from the first sensor signal;

computing a frequency response using the 90 degree phase shift and the first sensor signal;

determining a substantially instantaneous flow stream density of the gas flow material using the frequency response;

comparing the substantially instantaneous flow stream density to one or both of a predetermined gas density that is representative of a gas flow fraction of the gas flow material and a predetermined liquid density that is representative of a liquid flow fraction; and determining the liquid flow fraction from the flow stream density and one or both of the predetermined gas density and the predetermined liquid density.

17. The method of claim 16, further comprising determining the gas flow fraction.

18. The method of claim 16, with the determining the substantially instantaneous flow stream density from the frequency response comprising:

squaring the frequency response to generate a squared frequency response; and inverting the squared frequency response to generate the substantially instantaneous flow stream density.

19. The method of claim 16, further comprising:

comparing the liquid flow fraction to a predetermined liquid fraction threshold; and setting-an alarm-condition if the liquid flow fraction exceeds the predetermined liquid fraction threshold.

20. The method of claim 16, with the comparing further comprising comparing the substantially instantaneous flow stream density to a drive gain and to at least one of a predetermined gas density that is representative of a gas flow fraction of the gas flow material and a predetermined liquid density that is representative of a liquid flow fraction.

21. A method for determining a liquid flow fraction in a gas flow material flowing through a-flow meter, the method comprising:

receiving a first sensor signal and a second sensor signal from the flow meter;

generating a 90 degree phase shift from the first sensor signal;

computing a frequency response using the 90 degree phase shift and the first sensor signal;

determining a flow stream density of the gas flow material using the frequency response; and determining the liquid flow fraction from the flow stream density.

22. The method of claim 21, further comprising determining the gas flow fraction.

23. The method of claim 21, with the determining the flow stream density from the frequency response comprising:

squaring the frequency response to generate a squared frequency response; and inverting the squared frequency response to generate the flow stream density.

24. The method of claim 21, with the determining the liquid flow fraction further comprising:

comparing the flow stream density to at least one of a predetermined gas density that is representative of a gas flow fraction of the gas flow material and a predetermined liquid density that is representative of a liquid flow fraction; and determining the liquid flow fraction from the comparing.

25. The method of claim 21, further comprising:

comparing the liquid flow fraction to a predetermined liquid fraction threshold; and setting an alarm condition if the liquid flow fraction exceeds the predetermined liquid fraction threshold.

26. The method of claim 21, with the determining the liquid flow fraction further comprising determining the liquid flow fraction from the flow stream density and a drive gain.

\* \* \* \* \*